(12) United States Patent
Dokka et al.

(10) Patent No.: US 8,168,600 B2
(45) Date of Patent: May 1, 2012

US008168600B2

(54) COMPOSITIONS AND METHODS FOR TOPICAL DELIVERY OF OLIGONUCLEOTIDES

(75) Inventors: Sujatha Dokka, San Marcos, CA (US); Scott Cooper, Petaluma, CA (US); Susan Kelly, San Diego, CA (US); Gregory E. Hardee, San Diego, CA (US); James G. Karras, San Marcos, CA (US)

(73) Assignee: Isis Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 11/112,451

(22) Filed: Apr. 21, 2005

(65) Prior Publication Data

US 2005/0238606 A1 Oct. 27, 2005

Related U.S. Application Data

(60) Provisional application No. 60/565,244, filed on Apr. 23, 2004, provisional application No. 60/592,577, filed on Jul. 29, 2004.

(51) Int. Cl.
  C12N 15/11 (2006.01)
  A61K 48/00 (2006.01)
(52) U.S. Cl. ......................................................... 514/44
(58) Field of Classification Search ...................... 514/44
  See application file for complete search history.

(56) References Cited

U.S. PATENT DOCUMENTS

| | | | |
|---|---|---|---|
| 5,290,561 A | 3/1994 | Farhadieh et al. | |
| 5,641,508 A | 6/1997 | Li et al. | |
| 5,718,914 A | 2/1998 | Foldvari | |
| 5,906,822 A | 5/1999 | Samour et al. | |
| 5,914,126 A | 6/1999 | Li et al. | |
| 5,994,320 A * | 11/1999 | Low et al. | 514/44 |
| 6,010,715 A | 1/2000 | Wick et al. | |
| 6,111,094 A * | 8/2000 | Bennett et al. | 536/24.5 |
| 6,355,438 B1 * | 3/2002 | Baker et al. | 435/6 |
| 6,582,908 B2 | 6/2003 | Fodor et al. | |
| 6,841,539 B1 * | 1/2005 | Mehta et al. | 514/44 |
| 2004/0247555 A1 * | 12/2004 | Sprecher et al. | 424/70.14 |
| 2005/0096287 A1 * | 5/2005 | Mehta et al. | 514/44 |
| 2005/0260620 A1 | 11/2005 | Christiano et al. | |
| 2006/0270621 A1 | 11/2006 | Christiano | |

FOREIGN PATENT DOCUMENTS

| WO | WO 98/22031 | | 5/1998 |
|---|---|---|---|
| WO | WO 99/38965 | A1 | 8/1999 |
| WO | WO 02/083891 | A2 | 10/2002 |
| WO | WO 2004/063331 | A2 | 7/2004 |
| WO | WO 2004/093788 | A3 | 11/2004 |

OTHER PUBLICATIONS

Raghavachari et al, Journal of Pharmaceutical Sciences, 91:615-622, 2002.*
Cserhalmi-Friedman et al, Experimental Dermatology, 13:155-162, 2004.*
Fan et al, Nature Biotechnology, 17:870-872, 1999.*
Alexeev et al, Nature Biotechnology, 18:43-47, 2000.*
Hoffman, Journal of Drug Targeting, 5:67-74, 1997.*
Dokka et al, Dermal delivery of topically applied oligonucleotides via follicular transport in mouse skin. J Invest Dermatol. 124(5):971-5, 2005.*
Matsuzaki et al. Role of hair papilla cells on induction and regeneration processes of hair follicles, Wound Repair Regen., 6(6):524-30, 1998.*
White et al., Antisense oligonucleotide treatments for psoriasis, Expert Opin Biol Ther. 4(1):75-81, 2004.*
Harding, The stratum corneum: structure and function in health and disease, Dermatologic Therapy 17 suppl. 1: 6-15, 2004.*
Cotsarelis, G., "Les follicules pilaires comme cibles de la thérapie génique," Ann. Dermatol. Venereol. (2002) 129:841-844, Abstract only (in English).
Banga, A. J. et al., "Assessing the potential of skin electroporation for the delivery of protein-and gene-based drugs," TIBTECH (1998) 16:408-412.
Barry, B. W., "Novel mechanisms and devices to enable successful transdermal drug delivery," Eur. J. Pharm. Sci. (2001) 14:101-114.
Brand, R. M. et al., "Transdermal delivery of antisense compounds," Adv. Drug Delivery Rev. (2000) 44:51-57.
Cotsarelis, G., "Les follicules pilaires comme cibles de la thérapie génique," Ann. Dermatol. Venereol. (2002)129:841-844, Abstract only (in English).
Elias, P. M. et al., "Percutaneous Transport in Relation to Stratum Corneum Structure and Lipid Composition," J. Invest. Dermatol. (1981) 76(4):297-301.
Lauer, A. C. et al., "Transfollicular Drug Delivery," Pharm. Res. (1995) 12(2):179-186.
Lauer, A. C. et al., Evaluation of the Hairless Rat as a Model for in Vivo Percutaneous Absorption, J. Pharm. Sci. (1997) 86(1):13-18.
Li, L. et al., "Product-Delivering Liposomes Specifically Target Hair Follicles in Histocultured Intact Skin," In Vitro Cell. Dev. Biol. (1992) 28A:679-681.
Li, L. et al., "The feasibility of targeted selective gene therapy of the hair follicle," Nat. Med. (1995) 1(7):705-706.
Li, L. et al., "Liposomes can Specifically Target Entrapped Melanin to Hair Follicles in Histocultured Skin," In Vitro Cell. Dev. Biol. (1993) 29A:192-194.
Li, L. et al., "Liposome Targeting of High Molecular Weight DNA to the Hair Follicles of Histocultured Skin: A Model for Gene Therapy of the Hair Growth Process," In vitro Cell. Dev. Biol. (1993) 29A:258-260.
Li, L. et al., "Model of Selective Gene Therapy of Hair Growth: Liposome Targeting of the Active Lac-Z Gene to Hair Follicles of Histocultured Skin," In Vitro Cell. Dev. Biol. (1995) 31A:11-13.

(Continued)

Primary Examiner — Wu-Cheng Winston Shen
(74) Attorney, Agent, or Firm — Knobbe Martens Olson & Bear LLP

(57) ABSTRACT

The present invention relates to compositions and methods which enhance the delivery of nucleic acids and other nucleosidic moieties via topical routes of administration. The invention relates to the use of an aqueous solution to preferentially deliver nucleic acids preferentially to hair follicles. The invention relates to a method of inhibiting hair growth comprising administration of a nucleic acid preferentially to a hair follicle.

21 Claims, 3 Drawing Sheets
(3 of 3 Drawing Sheet(s) Filed in Color)

OTHER PUBLICATIONS

Lieb, L. M. et al., "Description of the Intrafollicular Delivery of Large Molecular Weight Molecules to Follicles of Human Scalp Skin In Vitro," *J. Pharm. Sci.* (1997) 86(9):1022-1029.

Mehta, R. C. et al., "Intercellular Adhesion Molecule-1 Suppression in Skin by Topical Delivery of Anti-Sense Oligonucleotides," *J. Invest. Dermatol.* (2000) 115:805-812.

Mezei, M. et al., "Liposomes—A selective drug delivery system for the topical route of administration: gel dosage form," *J. Pharm. Pharmacol.* (1982) 34:473-474.

Mrowietz, U., "The Enigma of Cyclosporin A Treatment of Psoriasis: Systemic Efficacy versus Topical Non-responsiveness," *Acta Derm. Venereol. (Stockh)* (1992) 72:321-326.

Regnier, V. et al., "Parameters Controlling Topical Delivery of Oligonucleotides by Electroporation," *J. Drug Targeting* (1998) 5(4):275-289.

Schmook, F. P. et al., "Penetration of Sandimmune (Cyclosporin A) in Rat Skin in vitro," *Skin Pharmacol.* (1993) 6:116-124.

Tezel, A. et al., "Synergistic Effect of Low-Frequency Ultrasound and Surfactants on Skin Permeability," *J. Pharm. Sci.* (2002) 91(1):91-100.

White, P. J. et al., "C-5 Propyne-Modified Oligonucleotides Penetrate the Epidermis in Psoriatic and Not Normal Human Skin After Topical Application," *J. Invest. Dermatol.* (2002) 118:1003-1007.

Zewert, T. E. et al., "Transdermal Transport of DNA Antisense Oligonucleotides by Electroporation," *Biochem. Biophys. Res. Commun.* (1995) 212(2):286-292.

Branch et al., "A good antisense molecule is hard to find," TIBS (1998) 23:45-50.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002, (one page).

Crooke et al., "Basic Principles of Antisense Therapeutics" Antisense Research and Application (1998) Chapter 1:1-50.

New England Biolabs 1998/99 Catalog (cover page and pp. 121 and 284).

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Griffiths et al., "Keratinocyte Intercellular Adhesion Molecule-1 (ICAM-1) Expression Preceedes Derman T Lymphocyte Infiltration in Allergic Contact Dermatitis (Rhus dermatitis)" Am. J. Pathology (1989) 135:1045-1053.

Hakugawa et al., "The Inhibitory Effect of Anti-Adhesion Molecule Antibodies on Eosinophil Infiltration in Cutaneous Late Phase Response in Balb/c Mice Sensitized with Ovalbumin (OVA)" J. Dermatol. (1997) 24:73-79.

Hegemann et al., "Biochemical Pharmacology of Protein Kinase C and its Relevance for Dermatology" Pharmcology of the Skin, Mukhtar, H. (eds.), CRC Press, Boca Raton (1992) 22:257-268.

McCullough et al., "Regulation of Epidermal Proliferation in Mouse Epidermis by Combination of Difluoromethyl Ornithine (DFMO) and Methylglyoxal Bis(guanylhdrazone) (MGBG)" J. Investigative Dermatology (1985) 85:518-521.

Nolen III et al., "Percutaneous penetration of methyl phosphonate antisense oligonucleotides" Intl. J. Pharm. (1994) 107:169-177.

Oldenburg et al., "Iontopheretic delivery of oligonucleotides across full thickness hairless mouse skin" Journal of Pharmaceutical Sciences (1995) 84(8):915-921.

Shiohara et al., "Fixed drug Eruption: Expression of Epidermal Keratinocyte Intercellular Adhesion Molecule-1 (ICAM-1)" Arch. Dermatol. (1989) 125:1371-1376.

\* cited by examiner

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 1
tccgtcatcg ctcctcaggg                                                 20

<210> SEQ ID NO 2
<211> LENGTH: 20
<212> TYPE: DNA
<213> ORGANISM: Artificial Sequence
<220> FEATURE:
<223> OTHER INFORMATION: Antisense Compound

<400> SEQUENCE: 2
ttgcttccat cttcctcgtc                                                 20

<210> SEQ ID NO 3
<211> LENGTH: 20
<212> TYPE: DNA
<213> ORGANISM: Artificial Sequence
<220> FEATURE:
<223> OTHER INFORMATION: Antisense Compound

<400> SEQUENCE: 3
gcccaagctg gcatccgtca                                                 20

<210> SEQ ID NO 4
<211> LENGTH: 20
<212> TYPE: DNA
<213> ORGANISM: Artificial Sequence
<220> FEATURE:
<223> OTHER INFORMATION: Antisense Compound

<400> SEQUENCE: 4
cccccaccac ttcccctctc                                                 20

<210> SEQ ID NO 5
<211> LENGTH: 20
<212> TYPE: DNA
<213> ORGANISM: Artificial Sequence
<220> FEATURE:
<223> OTHER INFORMATION: Antisense Compound

<400> SEQUENCE: 5
tgcatccccc aggccaccat                                                 20

<210> SEQ ID NO 6
<211> LENGTH: 20
<212> TYPE: DNA
<213> ORGANISM: Artificial Sequence
<220> FEATURE:
<223> OTHER INFORMATION: Antisense Compound

<400> SEQUENCE: 6
tccgtcatcg ctcctcaggg                                                 20

<210> SEQ ID NO 7
<211> LENGTH: 21
<212> TYPE: DNA
<213> ORGANISM: Artificial Sequence
<220> FEATURE:
<223> OTHER INFORMATION: Antisense Compound
```

```
<400> SEQUENCE: 7
gcgtttgctc ttcttcttgc g                                              21

<210> SEQ ID NO 8
<211> LENGTH: 20
<212> TYPE: DNA
<213> ORGANISM: Artificial Sequence
<220> FEATURE:
<223> OTHER INFORMATION: Antisense Compound

<400> SEQUENCE: 8
gttctcgctg gtgagtttca                                                20

<210> SEQ ID NO 9
<211> LENGTH: 15
<212> TYPE: DNA
<213> ORGANISM: Artificial Sequence
<220> FEATURE:
<223> OTHER INFORMATION: Antisense Compound

<400> SEQUENCE: 9
aacttgtgct tgctc                                                     15

<210> SEQ ID NO 10
<211> LENGTH: 20
<212> TYPE: DNA
<213> ORGANISM: Artificial Sequence
<220> FEATURE:
<223> OTHER INFORMATION: Antisense Compound

<400> SEQUENCE: 10
tcccgcctgt gacatgcatt                                                20

<210> SEQ ID NO 11
<211> LENGTH: 20
<212> TYPE: DNA
<213> ORGANISM: Artificial Sequence
<220> FEATURE:
<223> OTHER INFORMATION: Antisense Compound

<400> SEQUENCE: 11
gtgctcatgg tgcacggtct                                                20

<210> SEQ ID NO 12
<211> LENGTH: 20
<212> TYPE: DNA
<213> ORGANISM: Artificial Sequence
<220> FEATURE:
<223> OTHER INFORMATION: Antisense Compound

<400> SEQUENCE: 12
gtgtgccaga caccctatct                                                20

<210> SEQ ID NO 13
<211> LENGTH: 20
<212> TYPE: DNA
<213> ORGANISM: Artificial Sequence
<220> FEATURE:
<223> OTHER INFORMATION: Antisense Compound

<400> SEQUENCE: 13
gctgattaga gagaggtccc                                                20
```

```
<210> SEQ ID NO 14
<211> LENGTH: 20
<212> TYPE: DNA
<213> ORGANISM: Artificial Sequence
<220> FEATURE:
<223> OTHER INFORMATION: Antisense Compound

<400> SEQUENCE: 14
ttgcttccat cttcctcgtc                                                    20
```

COMPOSITIONS AND METHODS FOR TOPICAL DELIVERY OF OLIGONUCLEOTIDES

RELATED APPLICATIONS

This application claims priority to U.S. Provisional Patent Applications 60/565,244 and 60/592,577 filed on Apr. 23, 2004 and Jul. 29, 2004, respectively. Both applications are incorporated by reference herein in their entirety.

SEQUENCE LISTING

A paper copy of the sequence listing and a computer-readable form of the sequence listing, on diskette, containing the file named FMDL0008USSEQ.txt, which was created on Apr. 21, 2005, are herein incorporated by reference.

FIELD OF THE INVENTION

The present invention relates to compositions and methods for the topical delivery of nucleic acids to the hair follicle, and to other layers of the skin including the epidermis, the dermis, and strata therein, via the hair follicle. More particularly, the present invention is directed to the discovery that nucleic acids formulated in aqueous solution, without penetration enhancers, are targeted to the hair follicle. More specific objectives and advantages of the invention will hereinafter be made clear or become apparent to those skilled in the art during the course of explanation of preferred embodiments of the invention.

BACKGROUND OF THE INVENTION

Delivery of therapeutic agents to their site of action within the body is a challenge for most pharmaceutical agents. Oral administration requires that the agent be stable at the low pH of the stomach and readily absorbed in the intestine at a neutral pH. Administration of pharmaceutical agents by injection abrogates the need for agents that are stable through a wide pH range; however, a substantial portion of the agent may be eliminated from the circulation by the liver in what is known as the "first pass effect." Moreover, any route of injection (e.g. intravenous, subcutaneous) is a less desirable route of administration as compared to less invasive methods (e.g., topical, oral). This is especially true for agents that must be delivered on a relatively frequent basis, as injections are painful and require intervention of or training by a trained medical professional, sterile procedures, and methods to both obtain and discard needles in a safe manner.

Topical administration of pharmaceutical agents provides an ideal route of administration. The skin is substantially homogeneous, as compared to the digestive tract. Topical administration requires no special training or equipment, and is painless. However, uptake of pharmaceutical agents through the skin is limited due to the structure and function of the skin as a protective barrier.

Mammalian skin consists of two major, distinct layers, the epidermis and the dermis. The epidermis is comprised of the stratum corneum, the stratum granulosum, the stratum spinosum, and the stratum basale, with the stratum corneum being at the surface of the skin and the stratum basale being the deepest portion of the epidermis. The epidermis is between 50 μm and 0.2 mm thick, depending on its location on the body.

Beneath the epidermis is the dermis, which is significantly thicker than the epidermis. The dermis is primarily composed of collagen in the form of fibrous bundles. The collagenous bundles provide support for, inter alia, blood vessels, lymph capillaries, glands, nerve endings and immunologically active cells.

One of the major functions of the skin as an organ is to regulate the entry of substances into the body. The principal permeability barrier of the skin is provided by the stratum corneum, which is formed from many layers of cells in various states of differentiation. The spaces between cells in the stratum corneum is filled with different lipids arranged in lattice-like formations which provide seals to further enhance the skin's permeability barrier.

The permeability barrier provided by the skin is largely impermeable to molecules having molecular weight greater than about 750 Da. For larger molecules to cross the skin's permeability barrier, mechanisms other than normal osmosis must be used.

Several factors determine the permeability of the skin to administered agents. These factors include the characteristics of the treated skin, the characteristics of the delivery agent, interactions between both the drug and delivery agent and the drug and skin, the dosage of the drug applied, the form of treatment, and the post treatment regimen. To selectively target the epidermis and/or dermis, it is sometimes possible to formulate a composition with one or more penetration enhancers that enable penetration of the drug to a preselected stratum.

Nucleic acid based therapeutic agents are becoming more widely used as various mechanisms of modulating RNA and protein expression are discovered. A number of antisense oligonucleotide therapeutic agents are currently in clinical trials, and one antisense oligonucleotide based drug has been approved for use in humans (Vitravene). These oligonucleotides are single stranded molecules that are modified to increase their stability and/or affinity for their target RNA. More recently, the use of double stranded nucleic acid agents, known as small interfering RNAs (siRNAs) for the modulation of mRNA and protein expression has been described (Guo and Kempheus, Cell, 81:611-620, 1995). Montgomery et al. have shown that the primary interference effects of dsRNA are posttranscriptional (Montgomery et al., Proc. Natl. Acad. Sci. USA, 95:15502-15507, 1998). The posttranscriptional antisense mechanism defined in Caenorhabditis elegans resulting from exposure to double-stranded RNA (dsRNA) has since been designated RNA interference (RNAi). Antisense, RNAi and microRNA mechanisms rely substantially on specific base pairing of the nucleic acid therapeutic agent with the target mRNA of interest allowing for modulation of a specific target, typically decreasing the expression of an mRNA, subsequently reducing the expression of the corresponding protein. Nucleic acid based therapeutic agents that do not rely fully on base pairing to the target are also known, such as aptamers, G4 core sequences and ribozymes.

To date, nucleic acid based therapeutics have been delivered by injection, subcutaneously, intravenously or intravitreally. Both intravenous and intravetreal administration require the use of trained personnel to deliver the therapeutic agent. Although individuals may be taught to self-administer compositions by subcutaneous injection, it is not a preferred route of administration as discussed above. This places a practical limitation on the use of nucleic acid based therapeutics for relatively severe conditions (e.g. cancer) such that the individual to be treated is willing to undergo administration of the therapeutic agent by such an invasive manner. The ability to deliver nucleic acid therapeutic agents by non-invasive methods, such as topical administration, would make nucleic acid based therapeutics and agents useful for a far larger number of applications, including cosmetic uses (e.g. hair removal).

SUMMARY OF THE INVENTION

The invention includes the result that topically administered nucleic acids are taken up predominantly through hair follicles, before distribution throughout the skin. The invention further includes the result that topical administration of nucleic acids in an aqueous solution (e.g. saline), in the absence of penetration enhancers, results in the accumulation of nucleic acids in the hair follicle.

The invention includes a method for increasing delivery of nucleic acid molecules to hair follicles comprising application of a pharmaceutically acceptable composition comprising a nucleic acid, preferably in an aqueous solution, and topically applying the composition to skin wherein the skin contains hair follicles.

The invention includes a method for increasing uptake of a topically applied nucleic acid comprising applying the nucleic acid to skin having a relatively high concentration of hair follicles.

The invention includes a method for increasing systemic delivery of a nucleic acid by topical administration comprising applying the nucleic acid to skin having a relatively high concentration of hair follicles.

The invention comprises a method for delayed release of nucleic acid into the skin comprising topical application of nucleic acid to the skin in the absence of penetration enhancers, allowing sufficient time for the nucleic acid to be taken up into the hair follicles, and subsequently applying a penetration enhancer to the skin where the nucleic acid was administered, promoting release of the nucleic acid from the hair follicles into the skin.

In preferred embodiments of the methods of present invention, involve the administration of nucleic acids including, but not limited to, antisense oligonucleotides, aptamers, microRNA mimetics, or siRNAs.

The invention is a method for hair removal comprising topical administration of a nucleic acid in an aqueous solution to deliver the nucleic acid predominantly to the hair follicle. The nucleic acid to be delivered may comprise an oligonucleotide selected from an antisense oligonucleotide, an aptamer, a miRNA mimetic, or an siRNA targeting a nucleic acid encoding a gene including, but not limited to sonic hedgehog (Shh), the downstream transcription factor of Gli-2 that regulates Shh signaling, Gasdermin-3, RPB-J, ornathine decarboxylase (ODC), hepranase, vitamin D receptor, and hairless.

The invention is the use of a composition to deliver nucleic acid, such as an antisense oligonucleotide, an aptamer, a miRNA mimetic, or an siRNA to hair follicles wherein the composition comprises nucleic acid in an aqueous solution.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The numerous objects and advantages of the present invention can be better understood by those skilled in the art by reference to the accompanying figures, in which.

DETAILED DESCRIPTION AND PREFERRED EMBODIMENTS

Figure 1:
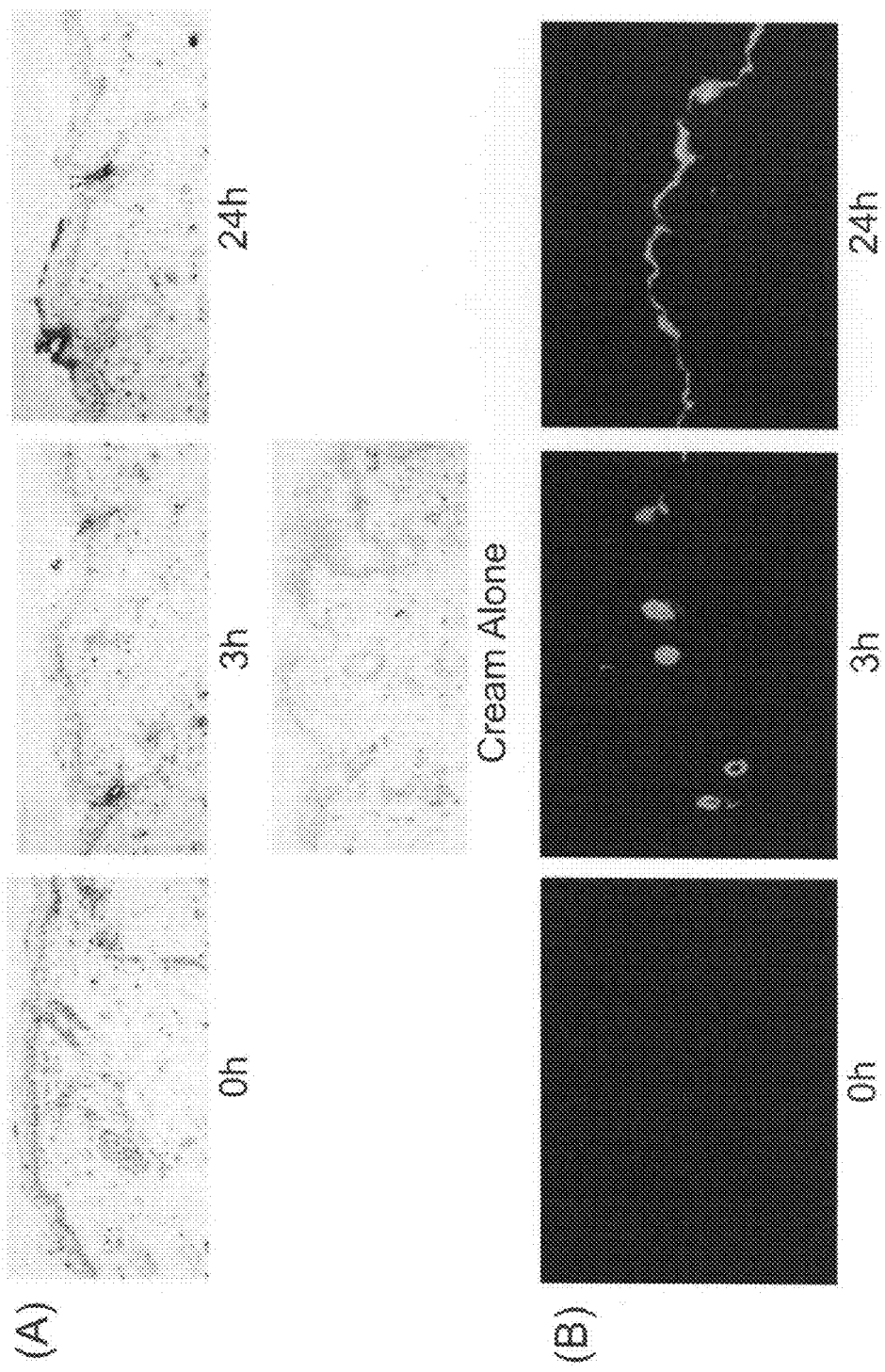
FIG. 1 shows the topical nucleic acid distribution after administration of cream to hairless mouse skin. (A) Immunohistochemical photomicrographs of 5% ISIS 13920 (SEQ ID NO: 1) cream formulation applied onto hairless mouse skin at 0 h, 3 h, and 24 h. Pictures taken at 10× magnification under Zeiss Axiolab microscope. Scale bar: 20 µm (B) FITC photomicrographs after topical application of 5% ISIS 18073 (SEQ ID NO: 2) cream formulation at 0 h, 3 h, and 24 h. Pictures taken at 40× magnification under Zeiss Axiolab microscope. Three animals were evaluated for each group. The micrographs show a representative section from one animal.

Local delivery of oligonucleotides to skin mediated by topically applied creams containing penetration enhancers is of interest for the therapy of inflammatory skin disease and possibly certain types of skin cancer, as well as cosmetic applications including promotion and inhibition of hair growth and modulation of skin pigmentation. Previous work showed that topically applied oligonucleotide was associated with living skin tissues, using both capillary gel electrophoresis and immunohistochemical techniques (Mehta R C et al. *J Invest Dermatol* 115: 805-812, 2000). Oligonucleotide accumulation in skin following topical application has been evaluated by several groups, with variable results apparently influenced by the chemical modifications incorporated into the sequence as well as the use of psoriatic or normal skin (Mehta R C et al. *J Invest Dermatol* 115: 805-812, 2000; Regnier V et al., *J Drug Target* 5: 275-289, 1998; White P J, et al., *J Invest Dermatol* 118: 1003-1007, 2002). Despite the demonstration of topical penetration into skin, the route of oligonucleotide transport through skin is unknown. Further understanding of this mechanism of transport would potentially aid in the development of better methodologies for topical oligonucleotide delivery.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. A discussion of antisense oligonucleotides and some desirable modifications can be found in De Mesmaeker et al. (*Acc.*

*Chem. Res.,* 1995, 28, 366). Generally, oligonucleotides formulated in the compositions of the invention may be from about 8 to about 100 nucleotides in length, more preferably from about 10 to about 50 nucleotides in length, and most preferably from about 10 about 25 nucleotides in length.

To this point, the published work evaluating oligonucleotide distribution in skin has utilized deoxyphosphorothioates or oligonucleotides containing the C-5 propyne modification (Mehta et al. *J Invest Dermatol* 115: 805-812, 2000; White et al. *J Invest Dermatol* 118: 1003-10072002). Current development of antisense therapeutics has focused on additional second-generation chemistries, particularly the 2'-O-methoxyethyl (MOE) sugar modification, due to its high affinity for target mRNA and enhanced resistance to nuclease degradation, compared to deoxyphosphorothioates, as well as its scaleable synthesis and emerging favorable safety profile (Altmann K H et al., *Biochem Soc Trans* 24: 630-637, 1996; Henry S et al, *J Pharmacol Exp Ther* 292: 468-479, 2000; Monia B P et al, *J Biol Chem* 268: 14514-14522, 1993). However, while this chemistry has provided improved antisense potency and longer half-life in vivo in liver and other tissues following systemic administration, little is known regarding its behavior in skin subsequent to topical application. Since MOE antisense oligonucleotides demonstrate similar protein binding characteristics to deoxyphosphorothioates, it would be expected that they would behave similarly in skin and therefore, most likely utilize a common route of transport.

To produce pharmacodynamic effects, oligonucleotides must penetrate the stratum corneum and reach the underlying tissues. Penetration of relatively large molecular weight, negatively charged molecules, such as cyclosporin, across intact stratum corneum is known to be limited (Mrowietz U, *Acta Derm Venereol* 72: 321-326, 1992; Schmook F P et al, *Skin Pharmacol* 6: 116-124, 1993), suggesting an inherent obstacle which must be overcome for oligonucleotides. A number of strategies have been implemented to achieve transdermal drug delivery, including the use of chemical entities that reversibly compromise the stratum corneum, microprojection arrays of various types for creating small channels through the skin surface, and the use of electric currents, and ultrasound (Banga A K, Prausnitz M R, *Trends Biotechnol* 16: 408-412, 1998; Brand R M, Iversen P L, *Adv Drug Deliv Rev* 44: 51-57, 2000; Mehta R C et al, *J Invest Dermatol* 115: 805-812, 2000; Regnier V et al, *J Drug Target* 5: 275-289, 1998; Tezel A et al, *J Pharm Sci* 91: 91-100, 2002; Zewert T E et al, *Biochem Biophys Res Commun* 212: 286-292, 1995). Other compositions and apparatuses have been developed for the delivery of therapeutic agents to the hair follicle including liposomes (Li, U.S. Pat. No. 5,641,508) and vibrational apparatus (Li, WO982203) The instant invention provides a method for the delivery of nucleic acids to hair follicles and/or other portions of the skin without the use of an apparatus.

In order to understand how oligonucleotides traffic in skin, and whether specific characteristics of skin might impact oligonucleotide localization, the behavior of topically applied oligonucleotides in either hairless or normal mice was investigated. One principle goal was to determine whether stratum corneum was indeed a major barrier to oligonucleotide transport through skin. In addition, the possibility of the exploitation of skin structures as a viable target tissue for nucleic acid delivery that could be reached without the need for biophysical approaches was analyzed. Kinetic analysis of oligonucleotide transport was performed, and the immunohistochemical and fluorescent staining patterns of oligonucleotides in mouse skin following topical application in aqueous and cream preparations were compared. The data indicate that topically applied oligonucleotides accumulate in the hair follicle and, in the presence of vehicles with a lipophyllic component, traffic into other layers of the skin, particularly the dermis.

Topical delivery of drug molecules is gaining increasing popularity for the treatment of dermatological diseases and for transdermal systemic delivery (Barry B W, *Eur J Pharm Sci* 14: 101-114, 2001; Brand R M, Iversen P L, *Adv Drug Deliv Rev* 44: 51-57, 2000). However topical delivery continues to be very challenging for most drug molecules because the human skin is a very effective barrier to chemical penetration. Consequently a number of strategies have been employed to overcome this barrier (Barry B W, *Eur J Pharm Sci* 14: 101-114, 2001). Recent research has shown that hair follicles and sebaceous glands may contribute significantly to topical and transdermal delivery (Cotsarelis G, *Ann Dermatol Venereol* 129: 841-844, 2002; Lauer A C et al, *Pharm Res* 12: 179-186, 1995; Li L and Hoffman R M, *Nat Med* 1: 705-706, 1995a). The total surface area of orifices of the pilosibaceous units occupies only about 0.1% of the total skin surface area. Hence, in the past there have been doubts on the significance of this pathway for delivery. However, certain areas of skin with a relatively high density of follicles, such as the face and scalp, can have as much as 10% of skin surface area. Secondly, even though hair follicle openings occupy only a small portion of the human skin surface area, they are invaginations of the epidermis, providing a much greater actual area for potential absorption below the skin surface (Lauer A C et al, *Pharm Res* 12: 179-186, 1995). It has also been suggested that the epidermis offers much lower resistance to polar drugs than the stratum corneum (Elias P M et al, *J Invest Dermatol* 76: 297-301, 1981). Hence, follicular delivery is gaining more and more attention as a viable route of transdermal/topical delivery.

The trafficking of antisense oligonucleotides in cream and aqueous formulations across mouse skin was analyzed and the results are disclosed herein. The delivery of nucleic acids across the skin of both hairless SKH1 mice and hairy Balb/c mice was analyzed. It has been observed that antisense oligonucleotides do not penetrate hairless mouse skin in the absence of penetration enhancers and/or lipophilic agents. However, the results were dramatically different when the same antisense oligonucleotide cream was applied to hair-clipped Balb/C mouse skin.

The compositions and methods of the invention are not limited by any specific mechanism of action. Implications of the data are discussed below. The performance of the experiments disclosed herein led to the surprising result that the hair follicle is a route of nucleic acid trafficking into skin following application of a topical formulation. These data are in agreement with other papers that have shown that large macromolecules could be delivered to skin via hair follicles (Li L et al, *In Vitro Cell Dev Biol Anim* 29A: 258-260, 1993a; Lieb L M et al, *J Pharm Sci* 86: 1022-1029, 1997). Following the kinetics of antisense oligonucleotide distribution in hairy Balb/c mice revealed that this localization was time-dependent. Dermal distribution of ASO was seen only with cream formulations, and not with simple saline formulations.

Most of the publications to date have shown delivery of large molecules to hair follicles via formulations such as liposomes (Li L and Hoffman R M, *Nat Med* 1: 705-706, 1995a; Li L and Hoffman R M, *In Vitro Cell Dev Biol Anim* 31: 11-13, 1995b; Li L et al, *In Vitro Cell Dev Biol Anim* 29A: 258-260, 1993a; Li L et al, *In Vitro Cell Dev Biol* 29A: 192-194, 1993b; Li L et al, *In Vitro Cell Dev Biol* 28A: 679-681, 1992). The disclosure herein is the first demonstration that antisense oligonucleotides when formulated in an aqueous solution accumulate in the hair follicle, and when formulated in a lipophilic cream, can distribute into the dermis via hair follicles. This is the first demonstration of the uptake of macromolecules into hair follicles in the absence of penetration enhancers or other lipophilic agents. It has been suggested that sebum, which flows into the hair follicle from the sebaceous duct, may necessitate a certain degree of lipophilicity for compounds to enter the hair follicles (Mezei M and Gulasekharam V, *J Pharm Pharmacol* 34: 473-474, 1982). The cream formulation presumably imparts a degree of lipophilicity, permitting delivery of antisense oligonucleotides through hair follicles into the dermis. Data published by Lauer et al suggests that the stratum corneum favors permeation of lipophilic compounds, whereas hair follicles favor penetration of polar compounds (Lauer A C et al, *J Pharm Sci* 86: 13-18, 1997). These data also indicate that both formulation differences and the relative number and functional integrity of the hair follicles play important roles in the trafficking behavior of topically applied antisense oligonucleotides. The data further demonstrate that the delivery of antisense oligonucleotides is dependent on the formulation rather than the chemistry of the nucleic acid.

"Topical administration" refers to the delivery of a nucleic acid to an animal by contacting, directly or otherwise, a formulation comprising the oligonucleotide to all or a portion of the skin (epidermis) of an animal. The term encompasses several routes of administration including, but not limited to, topical and transdermal. A common requirement for these modes of administration is penetration of the skin's permeability barrier and efficient delivery to the target tissue or stratum. In one aspect, topical administration is used as a means to penetrate the epidermis and dermis and ultimately achieve systemic delivery of oligonucleotides. In another aspect, topical administration is used as a means to selectively deliver oligonucleotides to the epidermis or dermis of an animal, or to specific strata thereof. Transdermal administration can take place via hair follicles.

Because of the advantages of topical delivery of drugs of the antisense class, the compositions and methods of the invention can be used in therapeutic methods as explained in more detail herein. The compositions and methods herein provided may also be used to examine the function of various proteins and genes in vitro in cultured or preserved dermal tissues and in animals. The invention can be thus applied to examine the function of any gene, including, in animal other than a human, those essential to animal development. The methods of the invention can also be used therapeutically or prophylactically, for example, for the treatment of animals that are known or suspected to suffer from diseases such as psoriasis, lichen planus, toxic epidermal necrolysis, ertythema multiforme, basal cell carcinoma, squamous cell carcinoma, malignant melanoma, Paget's disease, Kaposi's sarcoma, pulmonary fibrosis, Lyme disease and viral, fungal and bacterial infections of the skin.

The invention is drawn to the topical administration of a nucleic acid, such as an antisense oligonucleotide, having biological activity in an animal. By "having biological activity," it is meant that the nucleic acid functions to modulate the expression of one or more genes in an animal (e.g. by decreasing expression of a gene product). In the context of this invention, "to modulate" means to either effect an increase (stimulate) or a decrease (inhibit) in the expression of a gene. Such modulation can be achieved by, for example, an antisense oligonucleotide by a variety of mechanisms known in the art, including but not limited to transcriptional arrest; effects on RNA processing (capping, polyadenylation and splicing) and transportation; enhancement or reduction of cellular degradation of the target nucleic acid; and translational arrest (Crooke et al., *Exp. Opin. Ther. Patents,* 6:1, 1996).

The present invention provides methods and compositions for delivery of nucleic acids, particularly oligonucleotides, to the epidermis and/or dermis of an animal to increase the bioavailability of the nucleic acid therein. As used herein, the term "bioavailability" refers to the amount of the administered drug therapy (in this case the nucleic acid) that reaches and acts upon its target. The term is used for drugs whose efficacy is measured relative to the concentration in the blood even though the ultimate site of action of the drug might be outside the blood, e.g., intracellular (see van Berge-Henegouwen et al., *Gastroenterology,* 73:300, 1977).

The compositions and methods of the invention may be used for the prevention and/or amelioration and/or treatment of a disease, disorder, physical condition, including cosmetic condition (e.g. excessive hair growth, skin pigmentation, acne) that is treatable in whole or in part with one or more nucleic acids. In a preferred embodiment, such a disease, disorder or condition is treatable or manageable in whole or in part via topical administration of an antisense oligonucleotide to an animal having such a disease or disorder.

As used in the present invention, unless specified otherwise, the term "animal" refers to mammals including but not limited to humans and primates; avians including chickens and turkeys; domestic household, sport or farm animals including dogs, cats, sheep, goats, cows, horses and pigs; lab animals including rats, mice, rabbits and guinea pigs; fish; reptiles; and zoo animals.

The term "skin," as used herein, refers to the epidermis and/or dermis of an animal. The term "hair follicle" is defined as the structure from which hair grows. The methods and compositions of the instant invention can be used with hair follicles regardless of the location of the hair follicles on the body. For example, the methods and compositions can be used to deliver agents to hair follicles on the scalp, pubic areas, legs, face and back, as well as other parts of the body. An observer can readily determine areas of the body having a relatively high density of hair follicles by comparison of various parts of the body. Specific areas having relatively high hair follicle density may vary between individuals.

A preferred method for the delivery of biologically active substances to the skin is topical administration. Topical administration can be used as the route of administration when local delivery of a drug is desired at, or immediately adjacent to, the point of application of the drug composition or formulation. Three general types of topical routes of administration include administration of a drug composition to mucous membranes, skin or eyes.

Sustained release of a composition for topical administration may be achieved by the use of patches designed for transdermal drug delivery. Such patches are typically used for systemic delivery of therapeutic agents. Patches for such uses are well known to those skilled in the art (see e.g., U.S. Pat. Nos. 6,010,715; 5,718,914 and 5,290,561). The use of such patches is contemplated in the instant invention.

Pharmaceutical Compositions

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

Pharmaceutical compositions of the instant invention can be comprised of two components. The first component is an aqueous solution to deliver the nucleic acid to the hair follicles. It is applied to the skin in an area to be treated, preferably in an area of high hair follicle density. The second component is a penetration enhancer or other lipophilic agent suitable for topical administration. It is subsequently applied to promote migration of the nucleic acid from the hair follicle to other portions of the skin. Depending on the interval between the application of the two components to the skin, such compositions and method can be used for delayed release of the nucleic acid into the dermis and/or epidermis. Alternatively it would likely allow for presentation of higher concentration of the nucleic acid in the dermis and/or epidermis by first accumulating a relatively high concentration of nucleic acid in the hair follicle before release into other strata of the skin.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Preservatives used in any oligonucleotide formulation preferably have broad spectrum of antimicrobial activity and are compatible with highly negatively charged nucleic acids at neutral or near neutral pH. To determine preferred preservatives, oligonucleotides were incubated with various preservatives in the presence and absence of selected organisms [*Staphylococcus aureus* (ATCC No. 6538), *Escherichia coli* (ATCC No. 8739), *Candida albicans* (ATCC No. 10231) and *Aspergillus niger* (ATCC No. 16404)] according to USP 23 Antimicrobial Effectiveness Test (AET) procedures. According to results of these studies it has been discovered that preferred preservatives for oligonucleotide formulations include a combination of methylparaben, propylparaben and phenoxyethanol. The total amount of the preservative combination will depend on the dosage form used but will in general be from about 0.1% to 20% by weight. In topical formulations of the invention, the preservative combination will be present in an amount from about 0.1% to 10%, preferably 0.5% to 8% and more preferably 1% to 5%. In a preferred embodiment, methylparaben and propylparaben will each be present in an amount from about 0.1% to 1% and phenoxyethanol in an amount from about 1 to 5%. In a particularly preferred embodiment methylparaben, propylparaben and phenoxyethanol will be present in a ratio of about 1:1:5 respectively.

Penetration Enhancers

In one embodiment, the present invention may employ various penetration enhancers to affect the efficient delivery of nucleic acids, particularly oligonucleotides, to the skin of animals via hair follicles. Dogma states that usually only lipid soluble or lipophilic drugs readily cross cell membranes. However, the invention includes the surprising result that the uptake of nucleic acids into hair follicles occurs in aqueous solutions in the absence of penetration enhancers or other lipophilic agents. Penetration enhancers and lipophilic agent can be used to promote transport from the hair follicle to other portions of the skin (e.g. dermis and epidermis).

Penetration enhancers may be classified as belonging to one of five broad categories, i.e., surfactants, fatty acids, bile salts, chelating agents, and non-chelating non-surfactants (Lee et al., *Crit. Rev. Ther. Drug Carrier Systems*, p. 92, 1991). Each of the above mentioned classes of penetration enhancers are described below in greater detail. In the context of the instant invention, "penetration enhancers" include all agents that promote the transport of nucleic acids from the hair follicle to other portions of the skin. Such penetration enhancers may be selective for delivery to a specific layer of the skin or may promote transport from the hair follicle to all other portions of the skin.

Surfactants: In connection with the present invention, surfactants (or "surface-active agents") are chemical entities which, when dissolved in an aqueous solution, reduce the surface tension of the solution or the interfacial tension between the aqueous solution and another liquid, promoting absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Crit. Rev. Ther. Drug Carrier Systems*, p. 92, 1991); and perfluorhemical emulsions, such as FC-43 Takahashi et al., *J. Pharm. Pharmacol.*, 40:252, 1988).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Crit. Rev. Ther. Drug Carrier Systems*, p. 92, 1991; Muranishi, *Crit. Rev. Ther. Drug Carrier Systems*, 7:1, 1990; El Hariri et al., *J. Pharm. Pharmacol.*, 44:651, 1992).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics,* 9th Ed., Hardman et al. Eds., McGraw-Hill, New York, pages 934-935, 1996). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, page 92, 1991; Swinyard, Chapter 39 In: *Remington's Pharmaceutical Sciences,* 18th Ed., Gennaro, ed., Mack Publishing Co., Easton, Pa., 1990, pages 782-783; Muranishi, *Critical Reviews in Therapeutic Drug Carrier Systems,* 7:1, 1990; Yamamoto et al., *J. Pharm. Exp. Ther.,* 263:25, 1992; Yamashita et al., *J. Pharm. Sci.,* 79:579, 1990).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 618:315, 1993). Chelating agents of the invention include but are not limited to disodium ethylenediaminetetra-acetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, page 92, 1991; Muranishi, *Critical Reviews in Therapeutic Drug Carrier Systems*, 7:1, 1990; Buur et al., *J. Control Rel.*, 14:43, 1990).

Non-chelating non-surfactants: As used herein, non-chelating non-surfactant penetration enhancing compounds can be defined as compounds that demonstrate insignificant activity as chelating agents or as surfactants, but that enhance absorption of oligonucleotides through the alimentary mucosa (Muranishi, *Critical Reviews in Therapeutic Drug Carrier Systems*, 7:1, 1990). This class of penetration enhancers includes, for example, unsaturated cyclic ureas, 1-alkyl- and 1-alkenylazacyclo-alkanone derivatives (Lee et al., *Critical Reviews in Therapeutic Drug Carrier Systems*, page 92, 1991); and non-steroidal anti-inflammatory agents such as diclofenac sodium, indomethacin and phenylbutazone (Yamashita et al., *J. Pharm. Pharmacol.*, 39:621, 1987).

Agents that enhance uptake of oligonucleotides at the cellular level may also be added to the pharmaceutical and other compositions of the present invention. For example, cationic lipids, such as lipofectin (Junichi et al, U.S. Pat. No. 5,705, 188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115; Takakura et al., *Antisense & Nucl. Acid Drug Dev.*, 1996, 6, 177).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients suitable for non-parenteral administration that do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Aqueous Solutions

The instant invention includes compositions comprising nucleic acids in aqueous solutions. In a preferred embodiment the aqueous solution has about a physiological pH and salt concentration and includes components that are generally recognized as safe (GRAS) for use on humans and animals. In a more preferred embodiment, the final solution has a pH of at least about 6.0 to reduce depurination of the nucleic acid. The solutions preferably are comprised of a continuous aqueous phase wherein the salt and buffer concentrations can be modulated to allow for optimal solubility of the nucleic acid to be delivered. Such solutions and components are well known to those skilled in the art. Such solutions include, but are not limited to, buffered saline, including phosphate buffered saline, HEPES buffered saline, PIPES buffered saline, MES buffered saline and water. In a more preferred embodiment of the invention, the aqueous solution comprises a 0.9% normal saline solution. Appropriate aqueous solutions can be readily determined by those skilled in the art.

Other Components

The compositions of the present invention may additionally contain other adjunct components conventionally found in pharmaceutical compositions, at their art-established usage levels. For example, the compositions may contain additional, compatible, pharmaceutically-active materials such as, for example, antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously interact with the nucleic acid(s) of the formulation.

Aqueous suspensions may contain substances which increase the viscosity of the suspension including, for example, hydroxypropyl methylcellulose, sodium carboxymethylcellulose, sorbitol and/or dextran. The suspension may also contain stabilizers.

Nucleic Acid Therapeutics and Agents

The invention includes the delivery of nucleic acid therapeutics and agents including, but not limited to, antisense oligonucleotides, aptamers, microRNA mimetics, or siRNAs, to the hair follicles and possibly other strata of the skin. The exact function or mechanism of action of the nucleic acid delivered is not a limitation of the instant invention. The invention relies on the discovery that nucleic acids in aqueous solution accumulate preferentially in hair follicles; therefore, the invention is applicable to the delivery of all nucleotides regardless of their exact structure or intended use.

Chemically Modified Nucleic Acids

An oligonucleotide is a polymer of a repeating unit generically known as a nucleotide. An unmodified (naturally occurring) nucleotide has three components: (1) a nitrogen-containing heterocyclic base linked by one of its nitrogen atoms to (2) a 5-pentofuranosyl sugar and (3) a phosphate esterified to one of the 5' or 3' carbon atoms of the sugar. When incorporated into an oligonucleotide chain, the phosphate of a first nucleotide is also esterified to an adjacent sugar of a second, adjacent nucleotide via a 3'-5' phosphate linkage.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be further joined to form a circular structure, however, within the context of the invention, open linear structures are generally preferred.

Within the oligonucleotide structure, the phosphate groups are commonly referred to as forming the intersugar "backbone" of the oligonucleotide. The normal linkage or backbone of RNA and DNA is a 3' to 5' phosphodiester linkage. The backbone of an oligonucleotide (or other antisense compound) positions a series of bases in a specific order; the written representation of this ordered series of bases, usually written in 5' to 3' order unless otherwise indicated, is known as a nucleotide or nucleobase sequence.

Specific oligonucleotide chemical modifications are well known to those skilled in the art. It is not necessary for all positions in a given compound to be uniformly modified. In fact, chimeric molecules with more than one modification may be incorporated in a single antisense compound or even in a single residue thereof, for example, at a single nucleoside within an oligonucleotide. Modifications include modified linkages, modified nucleobases and modified sugars. Modifications can also include the addition of non-nucleic acid modifying groups, e.g., cholesterol, fluorescent tags, for targeting or detection of the oligonucleotide. Methods and compositions of the instant invention are not limited by the chemistry of the nucleic acid to be administered. Such nucleic acids may include any modifications that do not interfere with the binding of the nucleic acid to its target.

Modified Linkages: Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphos-phonates, thionoalklyphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus atom containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, certain of which are commonly owned with this application.

Preferred modified oligonucleotide backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application.

In other preferred oligonucleotide mimetics, both the sugar and the intersugar linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al. (*Science*, 1991, 254, 1497).

Most preferred embodiments of the invention are oligonucleotides with phosphorothioate backbones and oligonucleotides with heteroatom backbones, and in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Nucleobases: The compounds of the invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Id., pages 276-278) and are presently preferred base substitutions, even more particularly when combined with 2'-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, certain of which are commonly owned, and commonly owned U.S. patent application Ser. No. 08/762,488, filed on Dec. 10, 1996.

Sugar Modifications: The antisense compounds of the invention may additionally or alternatively comprise one or more substituted sugar moieties. Preferred oligonucleotides comprise one of the following at the 2' position: OH; F; O—, S—, or N-alkyl, O—, S—, or N-alkenyl, or O, S- or N-alkynyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy [2'-O—CH$_2$CH$_2$OCH$_3$, also known as 2'-O-(2-methoxyethyl) or 2'-MOE] (Martin et al., *Helv. Chim. Acta*, 1995, 78, 486), i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in co-owned U.S. patent application Ser. No. 09/016,520, filed on Jan. 30, 1998.

Other preferred modifications include 2'-methoxy(2'-O—CH$_3$), 2'-aminopropoxy(2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and commonly owned U.S. patent application Ser. No. 08/468,037, filed on Jun. 5, 1995.

Other Modifications: Additional modifications may also be made at other positions on the oligonucleotide, particularly the 3' position of the sugar on the 3' terminal nucleotide and the 5' position of 5' terminal nucleotide. For example, one additional modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-5-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys, Acta*, 1995, 1264, 229), or an octadecylamine or hexylamino-carbonyl-oxycholesterol moiety (Crooke et al., *J. Pharmacol. Exp. Ther.*, 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned.

Chimeric Oligonucleotides: The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate oligodeoxynucleotides hybridizing to the same target region, Cleavage of the RNA target can be routinely detected by gel electrophoresis and, if necessary, associated nucleic acid hybridization techniques known in the art. RNase H-mediated target cleavage is distinct from the use of ribozymes to cleave nucleic acids, and ribozymes are not comprehended by the present invention.

By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for, or stability when duplexed with, the target RNA molecule but are unable to support nuclease activity (e.g., 2'-fluoro- or 2'-methoxyethoxy-substituted). Other chimeras include "hemimers," that is, oligonucleotides in which the 5' portion of the oligonucleotide serves as a substrate for, e.g., RNase H, whereas the 3' portion is modified in such a fashion so as to have greater affinity for, or stability when duplexed with, the target RNA molecule but is unable to support nuclease activity (e.g., 2'-fluoro- or 2'-methoxyethoxy-substituted), or vice-versa.

A number of chemical modifications to oligonucleotides that confer greater oligonucleotide:RNA duplex stability have been described by Freier et al. (*Nucl. Acids Res.*, 1997, 25, 4429). Such modifications are preferred for the RNase H-refractory portions of chimeric oligonucleotides and may generally be used to enhance the affinity of an antisense compound for a target RNA.

Chimeric antisense compounds of the invention may be formed as composite structures of two or more oligonucleotides, modified oligonucleotides, oligonucleotides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned, and commonly owned and allowed U.S. patent application Ser. No. 08/465,880, filed on Jun. 6, 1995.

A further preferred modification includes 2'-dimethylamino oxyethoxy, i.e., a $O(CH_2)_2ON(CH_3)_2$ group, also known as 2'-DMAOE, as described in co-owned U.S. patent application Ser. No. 09/016,520, filed on Jan. 30, 1998. Other preferred modifications include 2'-methoxy(2'-O—$CH_3$), 2'-aminopropoxy(2'-O$CH_2CH_2NH_2$) and 2'-fluoro (2'-F). Similar modifications may also be made at other positions on the sugar group, particularly the 3' position of the sugar on the 3' terminal nucleotide or in 2'-5' linked oligonucleotides and the 5' position of 5' terminal nucleotide. The nucleosides of the oligo-nucleotides may also have sugar mimetics such as cyclobutyl moieties in place of the pentofuranosyl sugar.

Unsubstituted and substituted phosphodiester oligonucleotides are alternately synthesized on an automated DNA synthesizer (Applied Biosystems model 380B) using standard phosphoramidite chemistry with oxidation by iodine.

Phosphorothioates are synthesized as per the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270.

Alkyl phosphonate oligonucleotides are prepared as described in U.S. Pat. No. 4,469,863.

3'-Deoxy-3'-methylene phosphonate oligonucleotides are prepared as described in U.S. Pat. No. 5,610,289 or 5,625,050.

Phosphoramidite oligonucleotides are prepared as described in U.S. Pat. No. 5,256,775 or U.S. Pat. No. 5,366,878.

Alkylphosphonothioate oligonucleotides are prepared as described in published PCT applications PCT/US94/00902 and PCT/US93/06976 (published as WO 94/17093 and WO 94/02499, respectively).

3'-Deoxy-3'-amino phosphoramidate oligonucleotides are prepared as described in U.S. Pat. No. 5,476,925.

Phosphotriester oligonucleotides are prepared as described in U.S. Pat. No. 5,023,243.

Boranophosphate oligonucleotides are prepared as described in U.S. Pat. Nos. 5,130,302 and 5,177,198.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and PO or PS linkages are prepared as described in U.S. Pat. Nos. 5,378,825; 5,386,023; 5,489,677; 5,602,240 and 5,610,289.

Formacetal and thioformacetal linked oligonucleosides are prepared as described in U.S. Pat. Nos. 5,264,562 and 5,264,564.

Ethylene oxide linked oligonucleosides are prepared as described in U.S. Pat. No. 5,223,618.

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5. They may also be prepared in accordance with U.S. Pat. Nos. 5,539,082; 5,700,922, and 5,719,262.

Examples of specific oligonucleotides and the target genes which they inhibit, that may be employed in formulations of the present invention include:

TABLE 1

Examples of Modified and Chimeric Antisense Oligonucleotides

| ISIS NO | SEQUENCE | SEQ ID | TARGET |
|---|---|---|---|
| ISIS-2302 | GCCCA AGCTG GCATC CGTCA | 3 | ICAM-1 |
| ISIS-15839 | GCCCA AGCTG GCATC CGTCA | 3 | ICAM-1 |
| ISIS-1939 | CCCCC ACCAC TTCCC CTCTC | 4 | ICAM-1 |
| ISIS-2503 | TCCGT CATCG CTCCT CAGGG | 6 | Ha-ras |
| ISIS-2922 | GCGTT TGCTC TTCTT CTTGC G | 7 | HCMV |
| ISIS-13312 | GCGTT TGCTC TTCTT CTTGC G | 7 | HCMV |
| ISIS-3521 | GTTCT CGCTG GTGAG TTTCA | 8 | PKC-α |
| ISIS-9605 | GTTCT CGCTG GTGAG TTTCA | 8 | PKC-α |
| ISIS-9606 | GTTCT CGCTG GTGAG TTTCA | 8 | PKC-α |
| ISIS-14859 | AACTT GTGCT TGCTC | 9 | PKC-α |
| ISIS-5132 | TCCCG CCTGT GACAT GCATT | 10 | c-raf |
| ISIS-14803 | GTGCT CATGG TGCAC GGTCT | 11 | HCV |
| ISIS-28089 | GTGTG CCAGA CACCC TATCT | 12 | TNFα |
| ISIS-104838 | GCTGA TTAGA GAGAG GTCCC | 13 | TNFα |
| ISIS-2105 | TTGCT TCCAT CTTCC TCGTC | 14 | HPV | wherein (i) each oligo backbone linkage is a phosphorothioate linkage (except ISIS-9605) and (ii) each sugar is 2'-deoxy unless represented in bold font in which case it incorporates a 2'-O-methoxyethyl group and iii) underlined cytosine nucleosides incorporate a 5-methyl substituent on their nucleobase. ISIS-9605 incorporates natural phosphodiester bonds at the first five and last five linkages with the remainder being phosphorothioate linkages. Such modified nucleobases and linkages are well known to those skilled in the art.

Bioequivalents: In addition to oligonucleotide drugs per se, the pharmaceutical compositions of the present invention can be used to formulate any pharmaceutically acceptable salts, esters, or salts of such esters, or any other compound which, upon administration to an animal including a human, is capable of providing (directly or indirectly) a biologically active oligonucleotide or residue thereof. Additionally nucleic acid therapeutics can be delivered as prodrugs. Prodrugs are well known to those skilled in the art.

Therapeutic Indications and Other Uses

Psoriasis: One therapeutic indication of particular interest for topical delivery of oligonucleotides and other nucleic acids is psoriasis. Psoriasis is a common chronic and recurrent disease characterized by dry, well-circumscribed, silvery, scaling papules and plaques of various sizes. The disease varies in severity from a few lesions to widespread dermatosis with disabling arthritis or exfoliation. The ultimate cause of psoriasis is not known, but the thick scaling that occurs is probably due to increased epidermal cell proliferation (*The Merck Manual of Diagnosis and Therapy*, 15th Ed., pp. 2283-2285, Berkow et al., eds., Rahway, N.J., 1987). Inhibitors of Protein Kinase C (PKC), ICAM-1, STAT 3 and tumor necrosis factor (TNFα) have been shown to have both antiproliferative and anti-inflammatory effects in vitro. Some antipsoriasis drugs, such as cyclosporin A and anthralin, have been shown to inhibit PKC, and inhibition of PKC has been suggested as a therapeutic approach to the treatment of psoriasis (Hegemann, L. and G. Mahrle, *Pharmacology of the Skin*, H. Mukhtar, ed., pp. 357-368, CRC Press, Boca Raton, Fla., 1992). Antisense compounds targeted to Protein Kinase C (PKC) proteins are described in U.S. Pat. No. 5,620,963 to Cook et al. and U.S. Pat. No. 5,681,747 to Boggs et al.

Inflammation: Another type of therapeutic indication of particular interest for topical modes of delivery includes inflammatory disorders of the skin. These occur in a variety of forms including, for example, lichen planus, toxic epidermal necrolyis (TEN), ertythema multiforme and the like (*The Merck Manual of Diagnosis and Therapy*, 15th Ed., pp. 2286-2292, Berkow et al., eds., Rahway, N.J., 1987). Expression of ICAM-1 has been associated with a variety of inflammatory skin disorders such as allergic contact dermatitis, fixed drug eruption, lichen planus and psoriasis (Ho et al., *J. Am. Acad. Dermatol.*, 22:64, 1009; Griffiths et al., *Am. J. Pathology*, 135:1045, 1989; Lisby et al., *Br. J. Dermatol.*, 120:479, 1989; Shiohara et al., *Arch. Dermatol.*, 125:1371, 1989; Regezi et al., *Oral Surg. Oral Med. Oral Pathol.*, 81:682, 1996). Moreover, intraperitoneal administration of a monoclonal antibody to ICAM-1 decreases ovalbumin-induced eosinophil infiltration into skin in mice (Hakugawa et al., *J. Dermatol.*, 24:73, 1997). Antisense compounds targeted to ICAM-1 are described in U.S. Pat. Nos. 5,514,788 and 5,591,623, and co-pending U.S. patent application Ser. Nos. 09/009,490 and 09/062,416, Jan. 20, 1998 and Apr. 17, 1998, respectively, all to Bennett et al.

Other antisense targets for skin inflammatory disorders are VCAM-1 and PECAM-1. Intraperitoneal administration of a monoclonal antibody to VCAM-1 decreases ovalbumin-induced eosinophil infiltration into the skin of mice (Hakugawa et al., *J. Dermatol.*, 24:73, 1997). Antisense compounds targeted to VCAM-1 are described in U.S. Pat. Nos. 5,514,788 and 5,591,623. PECAM-1 proteins are glycoproteins which are expressed on the surfaces of a variety of cell types (for reviews, see Newman, *J. Clin. Invest.*, 99:3, 1997 and DeLisser et al., *Immunol. Today*, 15:490, 1994). In addition to directly participating in cell-cell interactions, PECAM-1 apparently also regulates the activity and/or expression of other molecules involved in cellular interactions (Litwin et al., *J. Cell Biol.*, 139:219, 1997) and is thus a key mediator of several cell:cell interactions. Antisense compounds targeted to PECAM-1 are described in U.S. Pat. No. 5,955,443, by Bennett et al.

Skin Cancers: Another type of therapeutic indication of interest for topical delivery of oligonucleotides encompasses a variety of cancers of the skin. Representative skin cancers include benign tumors (warts, moles and the like) and malignant tumors such as, for example, basal cell carcinoma, squamous cell carcinoma, malignant melanoma, Paget's disease, Kaposi's sarcoma and the like (*The Merck Manual of Diagnosis and Therapy*, 15th Ed., pp. 2301-2310, Berkow et al., eds., Rahay, N.J., 1987). A number of molecular targets involved in tumorigenesis, maintenance of the hyperproliferative state and metastasis are targeted to prevent or inhibit skin cancers, or to prevent their spread to other tissues.

The ras oncogenes are guanine-binding proteins that have been implicated in cancer by, e.g., the fact that activated ras oncogenes have been found in about 30% of human tumors generally; this figure approached 100% in carcinomas of the exocrine pancreas (for a review, see Downward, *Trends in Biol. Sci.*, 15:469, 1990). Antisense compounds targeted to H-ras and K-ras are described in U.S. Pat. No. 5,582,972 to Lima et al., U.S. Pat. No. 5,582,986 to Monia et al. and U.S. Pat. No. 5,661,134 to Cook et al., and in published PCT application WO 94/08003.

Protein Kinase C (PKC) proteins have also been implicated in tumorigenesis. Antisense compounds targeted to Protein Kinase C (PKC) proteins are described in U.S. Pat. No. 5,620,963 to Cook et al. and U.S. Pat. No. 5,681,747 to Boggs et al. Also of interest are AP-1 subunits and JNK proteins, particularly in regard to their roles in tumorigenesis and metastasis. The process of metastasis involves a sequence of events wherein (1) a cancer cell detaches from its extracellular matrices, (2) the detached cancer cell migrates to another portion of an animal's body, often via the circulatory system, and (3) attaches to a distal and inappropriate extracellular matrix, thereby created a focus from which a secondary tumor can arise. Normal cells do not possess the ability to invade or metastasize and/or undergo apoptosis (programmed cell death) if such events occur (Ruoslahti, *Sci. Amer.*, 275:72, 1996). However, many human tumors have elevated levels of activity of one or more matrix metalloproteinases (MMPs) (Stetler-Stevenson et al., *Annu. Rev. Cell Biol.*, 9:541, 1993; Bernhard et al., *Proc. Natl. Acad. Sci. (U.S.A.)*, 91:4293, 1994. The MMPs are a family of enzymes which have the ability to degrade components of the extracellular matrix (Birkedal-Hansen, *Current Op. Biol.*, 7:728, 1995). In particular, one member of this family, matrix metalloproteinase-9 (MMP-9), is often found to be expressed only in tumors and other diseased tissues (Himelstein et al., *Invasion & Metastasis*, 1994, 14, 246).

Several studies have shown that regulation of the MMP-9 gene may be controlled by the AP-1 transcription factor (Kerr et al., *Science*, 242:1242, 1988; Kerr et al., *Cell*, 61:267, 1990; Gum et al., *J. Biol. Chem.*, 271:10672, 1996; Hua et al., *Cancer Res.*, 56:5279, 1996). Inhibition of AP-1 function has been shown to attenuate MMP-9 expression (U.S. Pat. No. 5,985,558). AP-1 is a heterodimeric protein having two subunits, the gene products of fos and jun. Antisense compounds targeted to c-fos and c-jun are described in U.S. Pat. No. 5,985,558 by Dean et al.

Furthermore, AP-1 is itself activated in certain circumstances by phosphorylation of the Jun subunit at an amino-terminal position by Jun N-terminal kinases (JNKs). Thus, inhibition of one or more JNKs is expected to result in decreased AP-1 activity and, consequentially, reduced MMP expression. Antisense compounds targeted to JNKs are described in U.S. Pat. No. 5,877,309.

Infectious Diseases of the Skin: Also of interest for topical formulations of oligonucleotides are infectious diseases of the skin. Such infections are caused by viral, bacterial or fungal agents.

In the case of Lyme disease, the tick borne causative agent thereof, the spirochete *Borrelia burgdorferi*, up-regulates the expression of ICAM-1, VCAM-1 and ELAM-1 on endothelial cells in vitro (Boggemeyer et al., *Cell Adhes. Comm.*, 2:145, 1994). Furthermore, it has been proposed that the mediation of the disease by the anti-inflammatory agent prednisolone is due in part to mediation of this up-regulation of adhesion molecules (Hurtenbach et al., *Int. J. Immunopharmac.*, 18:281, 1996). Thus, potential targets for therapeutic mediation (or prevention) of Lyme disease include ICAM-1, VCAM-1 and ELAM-1 (supra).

Other infectious disease of the skin which are tractable to treatment using the compositions and methods of the invention include disorders resulting from infection by bacterial, viral or fungal agents (*The Merck Manual of Diagnosis and Therapy*, 15th Ed., pp. 2263-2277, Berkow et al., eds., Rahay, N.J., 1987). With regards to infections of the skin caused by fungal agents, U.S. Pat. No. 5,691,461 provides antisense compounds for inhibiting the growth of *Candida albicans*.

With regards to infections of the skin caused by viral agents, U.S. Pat. Nos. 5,166,195, 5,523,389 and 5,591,600 provide oligonucleotide inhibitors of Human Immunodeficiency Virus (HIV). U.S. Pat. No. 5,004,810 provides oligomers capable of hybridizing to herpes simplex virus Vmw65 mRNA and inhibiting its replication. U.S. Pat. Nos. 5,194,428 and 5,580,767 provide antisense compounds having antiviral activity against influenzavirus. U.S. Pat. No. 4,806,463 provides antisense compounds and methods using them to inhibit HTLV-III replication. U.S. Pat. Nos. 4,689,320, 5,442,049, 5,591,720 and 5,607,923 are directed to antisense compounds as antiviral agents specific to cytomegalovirus (CMV). U.S. Pat. No. 5,242,906 provides antisense compounds useful in the treatment of latent Epstein-Barr virus (EBV) infections. U.S. Pat. Nos. 5,248,670, 5,514,577 and 5,658,891 provide antisense compounds useful in the treatment of herpes virus infections. U.S. Pat. Nos. 5,457,189 and 5,681,944 provide antisense compounds useful in the treatment of papillomavirus infections. The antisense compounds disclosed in these patents, which are herein incorporated by reference, may be used with the compositions of the invention to effect prophylactic, palliative or therapeutic relief from diseases caused or exacerbated by the indicated pathogenic agents.

Cosmetic indications: The compositions and methods of the instant application allow for the administration of nucleic acid cosmetic and/therapeutic agents in a non-invasive manner. Nucleic acid agents can be used for a number of applications that may be considered therapeutic depending on the severity of the condition, including promotion or inhibition of hair growth. Such agents can also be used for modification of conditions such as skin pigmentation or acne. Other cosmetic applications can be envisioned by those skilled in the art.

The delivery of nucleic acid agents in aqueous solution allows for the limited and local delivery of agents to the hair follicle without substantial distribution throughout the skin, eliminating systemic exposure. By limiting exposure substantially to the hair follicle, the safety of the use of nucleic acid therapeutics is increased relative to delivery methods and formulations that allow for penetration of various strata of the skin. This allows for the use of agents that inhibit the expression of widely expressed genes (e.g. hairless (hr) which is expressed in the skin, brain, colon, retina, inner ear, cartilage and tooth) by preventing systemic exposure.

Modulation of a number of different genes can result in hair loss or growth. A candidate gene to target for modulation of hair growth is sonic hedgehog (Shh), or the downstream transcription factor Gli-2 that regulates Shh signaling. The hedgehog pathway is critical for hair follicle epithelial cell growth in the bulge region that regulates the hair cycle (St-Jacques, B et al., *Curr Biol* 8: 1058-1068, 1998; Mill, P et al., *Genes Dev* 17: 282-294, 2003). Gasdermin-3 was identified as the common target of two different mutations resulting in hairless phenotypes in mice (Lunny D P et al., *J Invest Dermatol* 124:615-621, 2005). RBP-J, a protease that cleaves the Notch family of receptors following ligand engagement and regulates cell fate in the hair follicle epithelium is an attractive target, as well (Yamamoto, N et al., *Curr Biol* 13: 333-338, 2003). Conditional ablation of RBP-J produced hair loss in mice, although epidermal cyst formation was also observed. Ornithine decarboxlyase (ODC), heparanase, and the Vitamin D receptor are also possible targets. ODC is a key enzyme in polyamine synthesis implicated in the anagen phase of the follicular growth cycle (Nancarrow, M J et al., *Mech Dev* 84: 161-164, 1999). Heparanase was found to enhance hair growth observed in transgenic mice following chemotherapy-induced hair loss, and its expression pattern in bulge keratinocytes further supports a role in hair growth (Zcharia, E et al., *Am J Pathol* 166: 999-1008, 2005). Vitamin D receptor deficient mice display an alopecia-like phenotype, and skin-specific rescue of hair growth can be achieved by a human Vitamin D transgene in this genetic background (Kong, J et al., *J Invest. Derm.* 118:631-638, 2002). Mice carrying a mutation in the hairless (hr) locus undergo rapid onset post-natal wave of hair shedding beginning at the age of 13-14 days. The hairless phenotype in mice is characterized by similar clinical and histological features in a rare form of human baldness (Djabali et al, *J. Cell Sci.* 114:367-376).

Modulation of skin pigmentation can be accomplished by altering expression of gene involved in the production of melanin.

Acne can be caused by a number of factors. Nucleic acid therapeutics targeted to inflammatory modulators can be useful in the treatment of the condition.

Systemic delivery: The compositions and methods of the instant invention can be used for systemic delivery of nucleic acid therapeutic agents for the treatment of systemic disease. Antisense oligonucleotides discussed above can be used for the treatment of inflammation, cancers and infections that are not limited to the skin. The compositions and methods of the instant invention allow for the uptake of nucleic acid based therapeutics into systemic circulation so that they can be delivered throughout the body. The invention is not limited to the prevention, amelioration and treatment of diseases of the skin. The ability to systemically deliver therapeutic nucleic acids using the compositions and methods of the instant invention would most likely be limited by the potency of the nucleic acid therapeutic rather than the compositions or methods.

Investigative Uses: Antisense oligonucleotides employed in the compositions of the present invention may also be used to determine the nature, function and potential relationship of various genetic components of the body to disease or body states in animals. Heretofore, the function of a gene has been chiefly examined by the construction of loss-of-function mutations in the gene (i.e., "knock-out" mutations) in an animal (e.g., a transgenic mouse). Such tasks are difficult, time-consuming and cannot be accomplished for genes essential to animal development since the "knock-out" mutation would produce a lethal phenotype. Moreover, the loss-of-function phenotype cannot be transiently introduced during a particular part of the animal's life cycle or disease state; the "knock-out" mutation is always present. "Antisense knockouts," that is, the selective modulation of expression of a gene by antisense oligonucleotides, rather than by direct genetic manipulation, overcomes these limitations (see, for example, Albert et al., *Trends in Pharmacological Sciences*, 1994, 15, 250). In addition, some genes produce a variety of mRNA transcripts as a result of processes such as alternative splicing; a "knock-out" mutation typically removes all forms of mRNA transcripts produced from such genes and thus cannot be used to examine the biological role of a particular mRNA transcript. Antisense oligonucleotides have been systemically administered to rats in order to study the role of the N-methyl-D-aspartate receptor in neuronal death, to mice in order to investigate the biological role of protein kinase C-α, and to rats in order to examine the role of the neuropeptide Y1 receptor in anxiety (Wahlestedt et al., *Nature*, 363:260, 1993; Dean et al., *Proc. Natl. Acad. Sci. U.S.A.*, 91:11762, 1994; and Wahlestedt et al., *Science*, 259:528, 1993, respectively). In instances where complex families of related proteins are being investigated, "antisense knockouts" (i.e., inhibition of a gene by systemic administration of antisense oligonucleotides) may represent the most accurate means for examining a specific member of the family (see, generally, Albert et al., *Trends Pharmacol. Sci.*, 15:250, 1994). By providing compositions and methods for the simple non-parenteral delivery of oligonucleotides and other nucleic acids, the present invention overcomes these and other shortcomings.

Treatment Regimens

The administration of therapeutic or pharmaceutical compositions for the prevention, amelioration or treatment of a disease or disease condition comprising the formulations of the invention is believed to be within the skill of those in the art.

From in vivo animal studies wherein oligonucleotides have been administered topically or intradermally it has been shown that oligonucleotides become widely distributed from the site of administration. For example oligonucleotide ISIS-2302 was topically applied on the back of mini pigs and rats. Samples of dermal and epidermal tissue analyzed by capillary gel electrophoresis and immunohistochemical staining detected significant levels of the oligonucleotide not only at the administration site (back) but also on stomach, neck and hind leg. Accordingly there is provided a method for delivering an oligonucleotide to a first dermal or epidermal tissue site in an animal comprising applying said oligonucleotide to a second dermal or epidermal tissue site in said animal wherein said first site is removed from said second site. In preferred embodiments, the oligonucleotide is administered topically in a pharmaceutical composition of the invention. The method is particularly useful for ensuring delivery of oligonucleotide evenly to dermal or epidermal tissue and/or over a great area or to sites that would otherwise be difficult to apply or would be sensitive to direct administration. This demonstrates the utility of topical administration of nucleic acids for systemic delivery.

EXAMPLES

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

Example 1

Oligonucleotides

Oligonucleotide Structure: The oligonucleotides used in the studies described herein have the following structures and biological activities.

ISIS 2302 is a 2'-deoxyoligonucleotide having a phosphorothioate backbone and the sequence 5'-GCC-CAA-GCT-GGC-ATC-CGT-CA-3' (SEQ ID NO:3). ISIS 2302 is targeted to the 3'-untranslated region (3'-UTR) of the human ICAM-1 gene. ISIS 2302 is described in U.S. Pat. Nos. 5,514, 788 and 5,591,623, hereby incorporated by reference.

ISIS 1939 is a 2'-deoxyoligonucleotide having a phosphorothioate backbone and the sequence 5'-CCC-CCA-CCA-CTT-CCC-CTC-TC-3' (SEQ ID NO:2). ISIS 1939 is targeted to the 3'-untranslated region (3'-UTR) of the human ICAM-1 gene. ISIS 1939 is described in U.S. Pat. Nos. 5,514,788 and 5,591,623, hereby incorporated by reference.

ISIS 15839 is a phosphorothioate isosequence "hemimer" derivative of ISIS 2302 having the structure 5'-GCC-CAA-GCT-GGC-ATC-CGT-CA-3' (SEQ ID NO:3), wherein emboldened "C" residues have 5-methylcytosine (m5c) bases and wherein the emboldened, double-underlined residues further comprise a 2'-methoxyethoxy modification (other residues are 2'-deoxy). ISIS 15839 is described in co-pending U.S. patent application Ser. No. 09/062,416, filed Apr. 17, 1998, hereby incorporated by reference.

ISIS 3082 is a 2'-deoxyoligonucleotide having a phosphorothioate backbone and the sequence 5'-TGC-ATC-CCC-CAG-GCC-ACC-AT-3' (SEQ ID NO:5). ISIS 3082 is targeted to the 3'-untranslated region (3'-UTR) of the murine ICAM-1 gene. ISIS 3082 is described in Stepkowski et al. (*J. Immunol.*, 1994, 153, 5336).

ISIS 2503 is a 2'-deoxyoligonucleotide having a phosphorothioate backbone and the sequence 5'-TCC-GTC-ATC-GCT-CCT-CAG-GG-3' (SEQ ID NO:6). ISIS 2503 is targeted to the translation initiation codon of the human oncogene, Ha-ras. ISIS 2503 is described in U.S. Pat. No. 5,576,208, hereby incorporated by reference.

ISIS 1939 (SEQ ID NO: 4), a phosphorothioate oligonucleotide targeted to a sequence in the 3-untranslated region of ICAM-1 mRNA has been found to exhibit significant biological activity. ISIS 2302 (SEQ ID NO: 3), which hybridizes to the ICAM-1 mRNA at a position 143 bases 3' to the ISIS 1939 target site was also found to be of similar activity in biological assays. Examination of the predicted RNA secondary structure of the human ICAM-1 mRNA 3'-untranslated region (Zuker, *Science*, 244:48, 1989) surprisingly suggested that both ISIS 1939 and ISIS 2302 hybridize to sequences predicted to be in a stable stem-loop structure of the mRNA. Dogma suggested that when designing antisense oligonucleotides regions of RNA secondary structure should be avoided. Thus, ISIS 1939 and ISIS 2302 would not have been predicted to inhibit ICAM-1 expression.

ISIS 2302 has been found to inhibit ICAM-1 expression in human umbilical vein cells, human lung carcinoma cells (A549), human epidermal carcinoma cells (A431), and human keratinocytes. ISIS 2302 has also demonstrated specificity for its target ICAM-1 over other potential nucleic acid targets such as HLA-α and HLA-β.

Both ISIS 2302 (SEQ ID NO: 3) and ISIS 1939 (SEQ ID NO: 4) markedly reduced ICAM-1 expression, as detected by northern blot analysis to determine mRNA levels, in C8161 human melanoma cells.

In an experimental metastasis assay, ISIS 2302 decreased the metastatic potential of C8161 cells, and eliminated the enhanced metastatic ability of C8161 cells resulting from TNF-α treatment. ISIS 2302 has also shown significant biological activity in animal models of inflammatory disease. The data from animal testing has revealed strong anti-inflammatory effects of ISIS 2302 in a number of inflammatory diseases including Crohn's disease, rheumatoid arthritis, psoriasis, ulcerative colitis, and kidney transplant rejection. When tested on humans, ISIS 2302 has shown good safety and activity against ulcerative colitis.

Example 2

In Vitro Skin Testing

Male and female hairless SKH1 mice 6-8 weeks old were obtained from Charles River Laboratories (Wilmington, Mass.) and were euthanized using carbon dioxide asphyxiation. Fresh and frozen skins were mounted on a vertical Franz diffusion cell (Permegear, N.J.) with each skin having a diffusional area of 0.636 $cm^2$. Receptor chambers having a volume of 5.1 ml were filled with isotonic phosphate buffer (pH 7.2) containing 0.1% (v/v) of 36% aqueous formaldehyde as preservative. Receptor temperatures were maintained at 37±0.5° C. and stirred continuously at 600 rpm. The skins were allowed to hydrate for 1 hour prior to starting an experiment. Experiments generally were performed at 24 hours.

Penetration enhancers/vehicles were added into the donor compartment for 1 hour and then washed off with 500 μl of methanol. The total amount of enhancer/vehicle that was added to each donor compartment was 10 μl (unless otherwise noted). After methanol wash, the skin was lightly wiped and blown dry to remove any visible moisture. In an experiment studying the effect of methanol on penetration enhancement, no wash was performed. Also, in experiments studying the effects of pretreatment time, the amount of time the enhancer was allowed to stay on the skin was varied (i.e., 30 minutes or 1, 2 or 3 hours).

Oligonucleotide [i.e., ISIS 2302 (SEQ ID NO: 3)] was added on top of the enhancer solution. ISIS 2302 was added to each donor compartment as a 200 μl normal saline solution containing both 1 mg of unlabeled oligonucleotide and approximately 300,000 decays per minute ("DPM") of radiolabeled oligonucleotide. Epidermal, dermal and receptor penetration values are expressed as the ratio of the counts penetrated versus the control counts.

The following chemicals were used as enhancers/vehicles: propylene glycol (PG), dimethyl sulfoxide (DMSO), isopropyl myristate (IPM), Azone, MIGLYOL™ 818, oleic acid, d-limonene, limonene, 1-dodecyl-2-pyrrolidinone (Idodecyl2pyrrol), 1-methyl-2-pyrrolidinone (1Methyl2pyrrol), menthone, ethanol and TWEEN 40.

Statistical analyses were performed on Excel using Students t-test (two-sample assuming equal variances) along with averages, standard deviations, and standard errors. Female hairless mice were preferentially used as the studies progressed due to an uncharacterized but recurring follicular infection that appeared to preferentially target male mice.

The best epidermal penetration enhancers for the delivery of Isis 2302 are isopropyl myristate ("IPM"; 1.67%, 2.14% and 3.11%), menthone (2.93%), ethylene glycol (2.41%), 1-methyl-2-pyrrolidinone ("1Methyl2pyrrol"; 2.41%), d-limonene (1.55%), MIGLYOL 818® (1.62%) and dimethyl sulfoxide (DMSO; 1.56%). In contrast, for dermal penetration, the best penetration enhancers are Tween 40 (1.42%), oleic acid (~1.0%), d-limonene (0.72%), 1-dodecyl-2-pyrrolidinone ("Idodecyl2pyrrol"; 0.67%), DMSO (0.38%) and 1-methyl-2-pyrrolidinone ("1Methyl2pyrrol"; 0.25%). There is no little or no correlation between epidermal penetration enhancement and dermal penetration enhancement, an effect which may be due to different mechanisms of action of delivery to the two layers, rates of penetration, the duration of the experiments, the duration of enhancer pretreatments, or a combination of such factors.

Experiments with Azone were carried out to examine how much of a factor methanol is in the delivery of Isis 2302. Azone pretreatment with a methanol wash resulted in epidermal and dermal penetration values of 1.31% and 0.16%, respectively, whereas the values for experiments without methanol values were 0.72% and 0.13% for epidermal and dermal penetration, respectively. Ethanol had little effect on the penetration of ISIS 2302 when limonene was used as an enhancer. Higher volumes of limonene and isopropyl myristate did not result in an increase in the penetration.

These data demonstrate that nucleic acids can be taken up through skin in the absence of hair follicles in the presence of penetration enhancers.

Example 3

Cream Formulations and Effects of Oligonucleotide Chemistries

Studies were carried out to optimize the formulation containing isopropyl myristate. Duration of pretreatment ranging from 30 minutes to 3 hours had little effect on the penetration of ISIS 2302. Lower concentration of isopropyl myristate in the range of 10 to 35% v/v in water reduced the penetration significantly; however, the coarse mixture of isopropyl myristate and water applied in very small quantities (10-30 μL) may have resulted in spotty coverage of the skin. Lower amounts of ISIS 2302 resulted in an increase in the percent of applied dose penetrated.

In order to formulate a cream from isopropyl myristate, its viscosity was increased using oil soluble agents and surfactants such as glyceryl monosterate, stearic acid and bees wax. Oligonucleotide was dissolved in a water phase consisting of aqueous surfactants and viscosity imparting agents such as polyoxyl-40 stearate and polyethylene glycol derivatives. Cream formulations consisting of water (36-45% w/w), isopropyl myristate (30-48% w/w), glyceryl monostearate (10-16% w/w), Polyoxyl-40 stearate (0-15% w/w) and antimicrobial preservatives (benzyl alcohol, methylparaben, propylparaben) were studied in vitro for penetration. Oligonucleotide was thoroughly mixed with the cream formulations to give a final concentration of 1 mg oligonucleotide for each 149 mg cream. Appropriate controls were used to determine the radioactivity per mg of cream.

The cream formulation with 30% isopropyl myristate resulted in an epidermal penetration of 1.66% and a dermal penetration of 1.57% for ISIS 2302. Similar penetration values were seen with cream formulation containing 48% isopropyl myristate.

A cream formulation of ISIS 15839, a 5-methylcytosine-comprising 2'-methoxyethoxy isosequence hemimer derivative of ISIS 2302, with 30% isopropyl myristate showed a very high dermal penetration, i.e., 11% of the applied dose. The results demonstrate that oligonucleotides of different chemical compositions penetrate the skin in the same formulation.

Example 4

In Vivo Testing of ICAM-1 Suppression

The oligonucleotide ISIS 3082 (SEQ ID NO:5), which is targeted to the murine ICAM-1 gene, was mixed with empty ("f") liposomes or encapsulated into ("e") liposomes as set forth below to determine the degree of ICAM-1 suppression effected thereby:

1. DOPE-f Liposomes (DOPE:DPPC:Chol; 20:60:20% w/w) mixed with ISIS 3082 to obtain 10 mg/mL ISIS 3082;
2. ISIS 3082 solution at 10 mg/mL;
3. DOPE-f Liposomes (DOPE:DPPC:Chol; 20:60:20% w/w) mixed with ISIS 3082 to obtain 10 mg/mL ISIS 3082;
4. DOPE-e Liposomes (DOPE:DPPC:Chol; 20:60:20% w/w) with ISIS 3082 encapsulated in the liposomes, not purified, to obtain 10 mg/mL ISIS 3082;
5. DMPG-f Liposomes (DMPG:DPPC:Chol; 20:60:20% w/w) mixed with ISIS 3082 to obtain 10 mg/mL ISIS 3082;
6. DMPG-e Liposomes (DMPG:DPPC:Chol; 20:60:20% w/w) with ISIS 3082 encapsulated in the liposomes, not purified, to obtain 10 mg/mL ISIS 3082;
7. DMPC-f Liposomes (DMPC:DPPC:Chol; 20:60:20% w/w) mixed with ISIS 3082 to obtain 10 mg/mL ISIS 3082;
8. DMPC-e Liposomes (DMPC:DPPC:Chol; 20:60:20% w/w) with ISIS 3082 encapsulated in the DMPC liposomes, not purified, to obtain 10 mg/mL ISIS 3082;
9. No treatment, phorbol myristate acetate ("PMA") positive control; and
10. No treatment, no PMA control ("basal").

Liposome Preparation: The liposomes were prepared by hydrating a dry film of lipids in a glass container with either phosphate buffered saline at pH 7.4 or a 10 mg/mL solution of ISIS 3082 in PBS. The hydrated lipids were then extruded 21 times through a 50 nm membrane to form small liposomes with final lipid concentration of ~100 mg/mL, drug concentration of ~10 mg/mL and particle size of ~100 nm.

Animal Studies: Liposome formulations were applied to the back of hairless mice using a Hilltop™ chamber (Hilltop Research, Cincinnati, Ohio) that keeps the formulation in place. Three mice were tested in each group. Forty-eight hours after the formulation application, the treated part of the skin was challenged with PMA to induce ICAM-1. Mice were sacrificed 4 hours after PMA application and skin collected for Northern analyses of the mRNA levels, which were performed essentially according to the protocol detailed in Examples 3 and 7 of co-pending U.S. patent application Ser. No. 09/062,416, filed Apr. 17, 1998, hereby incorporated by reference.

The results with ISIS 3082 mixed with empty liposomes are as follows:

| Formulation | Relative mRNA Level (PMA = 100%) |
|---|---|
| Basal | 12.46 ± 2.39 |
| DOPE-f (#1) | 71.80 ± 7.93 |
| DOPE-f (#2) | 64.02 ± 11.32 |
| DMPG-f | 63.84 ± 11.54 |
| DPPC-f | 91.80 ± 0.25 |
| PBS | 93.91 ± 11.04 |

The DOPE and DMPG liposomes show about 30% to about 40% reduction in PMA-induced ICAM-1 expression, whereas the phosphate buffered saline solution formulation and DPPC liposomes show much lower reduction. The results prove that ISIS 3082 penetrates the skin when mixed with liposomes and that the penetration of drug thus achieved is sufficient to cause a biological effect.

The results with ISIS 3082 encapsulated in the liposomes are as follows:

| Formulation | Relative mRNA Level (PMA = 100%) |
|---|---|
| Basal | 12.46 ± 2.39 |
| DOPE-e | 69.95 ± 5.19 |
| DPPC-e | 67.19 ± 11.99 |
| DMPG-e | 58.54 ± 12.40 |

The liposome formulations comprising DOPE, DPPC or DMPG and encapsulating ISIS 3082 all show a 30-50% reduction in ICAM-1 mRNA, showing that ISIS 3082 penetrates the skin when encapsulated in liposomes and that the penetration of drug thus achieved is sufficient to cause a biological effect.

These data demonstrate that transdermal delivery of nucleic acid to the skin of hairless mice in aqueous solution is minimal. Uptake is substantially enhanced by the presence of lipophilic agents.

Example 5

Comparison of Topical and Systemic Administration of Oligonucleotides

In order to develop a formulation for the local delivery of oligonucleotides via topical administration, the following experiments were carried out.

Formulations: A cream formulation of 2% ISIS 2503 (SEQ ID NO: 6), intended for topical application, was compared to 20 mg/mL formulations in saline administered via intravenous, subcutaneous or intradermal means.

The cream formulation was prepared by heating the oil phase [containing isopropyl myristate (30% w/w) and glyceryl monostearate (10% w/w)] and the aqueous phase [containing water (45% w/w) and polyoxyl-40-stearate (15% w/w)] to 70° C. followed by homogenization at 7,000 rpm using a Silverson L4RT mixer (Silverson Machines, East Long Meadows, Mass.), after which the mixture was allowed to cool to room temperature. The particle size of the oil phase droplet in the cream had a mean diameter of 1.0 um. ISIS 2503 was mixed with the cream by trituration.

Animal Studies: SCID mice (Taconic Farms, Inc., Germantown, N.Y.) ~6 weeks old, were transplanted with human skin and allowed to establish the xenograft for 6 weeks. 200 mg cream or 20 mg/kg solution were administered at 48, 24 and 4 hours prior to TNF-α administration. TNF-α was injected in to the xenograft to induce inflammation. Mice were sacrificed and skin isolated for immunohistochemistry.

Stained tissue samples show a pronounced accumulation of the oligonucleotides in the nuclei of the cells in the viable epidermis upon treatment with the cream formulations. Accumulation is also seen in the dermis but no nuclear accumulation is visible. The cream formulation thus provides for the selective delivery of oligonucleotides to cells of the dermis.

In contrast, photomicrographs of skin treated intravenously with the solution formulation show accumulation of oligonucleotide in the dermis but no nuclear accumulation is visible. There was no accumulation in the epidermis.

Similarly, photomicrographs of skin treated intradermally with the solution formulation show a large amount of oligonucleotide in the proximity of the needle tract in the dermis and some in the epidermis. Again, however, there is no nuclear accumulation.

Taken together, the preceding results show that oligonucleotide delivered to the dermis by systemic or direct injection route does not accumulate in the cells of viable epidermis whereas topical delivery with the cream formulation can target the viable epidermis. The cream formulation can thus be used to prepare pharmaceutical and other formulations comprising any of a variety of oligonucleotides, including but not limited to those described herein, intended for dermal delivery. The invention thus provides methods for preventing or treating a variety of dermal disease and disorders, such methods comprising contacting the skin of an animal with a pharmaceutical composition comprising an oligonucleotide according to the present disclosure.

Example 6

Follicular Transport of Topically Applied Oligonucleotides in Mouse Skin

In order to exhibit anti-inflammatory effects, antisense oligonucleotides, which are large anionic molecules, must penetrate the stratum corneum and reach the living epidermis and dermis. Topically applied deoxyphosphorothioate ASO targeted to ICAM-1 modulates cytokine-inducible target gene expression in engrafted human skin. The following experiment demonstrates the topical route of antisense entry into mouse skin using topical cream-based formulations and fluorochrome-tagged or naked second-generation 2'-O-methoxyethyl-modified oligonucleotides that react specifically with an antibody. In hairless mouse skin, immunohistochemical analysis and fluorescence microscopy were unable to detect the presence of oligonucleotide in epidermis or dermis following topical application using several doses and schedules although clear immunostaining was observed on the external surface of the stratum corneum and FITC-labeled oligonucleotide was observed in hair follicles. Kinetic analysis of oligonucleotide trafficking in hair-clipped Balb/c mouse skin following topical application using immunohistochemistry showed early follicular localization and subsequent accumulation in the dermis. Topical administration in saline resulted in oligonucleotide remaining within the hair follicle. These results were confirmed using a FITC-labeled oligonucleotide which showed diffusion of oligonucleotide from the midfollicle, suggesting that oligonucleotide transport through the skin involves a follicular route and further, that topical oligonucleotide therapy may be particularly well-suited for altering physiology within the hair follicle and related structures.

Oligonucleotide Selection and Formulation

All oligonucleotides used in these studies were second-generation chemistries containing the 2'-O-methoxyethyl (MOE) sugar modification. ISIS 13920 (SEQ ID NO: 1) was chosen as an immunohistochemistry marker for these distribution studies since it is easily recognized by a specific antibody as described below. ISIS 18073 is a fluorescently labeled ASO that enables detection by fluorescence microscopy. Synthesis and purification was performed as previously described (Monia B P et al, *J Biol Chem* 267: 19954-19962, 1992; Monia B P et al., *J Biol Chem* 268: 14514-14522, 1993).

For oligonucleotides formulated in cream, the following composition was used in these studies: glyceryl monostearate (10%), hydroxypropyl methylcellulose (0.5%), isopropyl myristate (10%), methylparaben (0.5%), propylparaben (0.5%), polyoxyl-40-stearate (15%) and water.

In Vivo Mouse Dermal Delivery.

The animals used in all studies were 6 to 8 week old hairless SKH1 or Balb/C mice (Charles River Laboratories Inc., Wilmington, Mass.). All studies were conducted utilizing protocols and methods approved by the Institutional Animal Care and Use Committee and carried out in accordance with the Guide for the Care and Use Committee of Laboratory Animals adopted and promulgated by the U. S. National Institutes of Health. All animals were provided food and water ad libitum and kept on 12 hour light/dark cycle.

Dermal Application.

Balb/c mice were hair-clipped the day before the experiment while avoiding cuts to the skin and cream was applied to the clipped area 24 hours later. Approximately 100 µl of 5% ISIS 13920 or 18073 (SEQ ID NO: 2) ASO containing cream was applied over an area of approximately 12 $cm^2$ on the dorsal surface of the skin. The formulation was rubbed onto the skin to ensure uniform distribution. Immediately after the treatment period, application sites were cleaned of residual cream with a mild surfactant (2% Tween 80 in water). Three mice were killed by exsanguination per time point and skin samples were collected. For saline formulations, 100 µl of 5% ASO containing a sterile normal saline solution (0.9%) was applied to the area and rubbed into the skin.

Histological Evaluation

Skin samples were carefully washed with 2% Tween 20 in PBS to remove any excess cream and fixed in 10% neutral buffered formalin for 24 hours before transferring to 70% ethanol for dehydration and storage. The tissues were embedded in paraffin and sectioned at 4 microns for analysis. The sections were deparaffinized in xylene and hydrated through graded alcohols for oligonucleotide (ODN) immunostaining and hematoxylin and eosin (H&E) stains. The affinity purified antibody used in this work, 2E1-B5 (Berkeley Antibody Company, Berkeley, Calif.), is an IgG1 which specifically recognizes a CG or TCG motif in phosphorothioate oligonucleotides. Endogenous peroxidase activity was quenched with peroxidase blocking reagent (Dako Corporation, Carpenteria, Calif.) for 10 minutes; sections were rinsed with PBS and treated with proteinase K (Dako) for 20 minutes. After blocking with normal donkey serum, (Jackson Laboratories, Burlingham, AB), sections were incubated for 1 hour with 2E1 monoclonal antibody diluted at 1:1000. After rinsing, the antibody was detected using HRP-donkey anti-mouse IgG F(ab)'2 diluted 1:100 (Jackson) for 1 hour. DAB (3,3'-diamino-benzidene, Dako) was used as a substrate. The tissue sections were counterstained with hematoxylin, dehydrated and mounted with coverslips. Serial sections of the tissues were stained with hematoxylin and eosin for routine histopathological analysis.

Tissue sections were blinded and ISIS 13920 immunostaining was evaluated using a Zeiss Axiolab microscope with a Sony color video camera at various magnifications up to 200×.

Antisense Oligonucleotide Distribution by FITC Staining

An 8 mm punch skin biopsy containing FITC labeled ISIS 18073 was obtained and placed in a labeled cryomold and covered with OCT (O.C.T. Compound VWR Cat.#25608-930). The mold containing the biopsy was gently submerged in a pre-chilled dewar flask containing liquid nitrogen/dry ice slurry for approximately one minute until O.C.T turned white and opaque. Tissue was stored in a −70 degree freezer until sections were cut. Tissue was allowed to come to a −20 degree temperature before cutting in a Leica CM 3050 cryostat at 5 microns. Sections were picked up on "+" superfrost slides and allowed to air dry for 4 hours. Sections were then fixed in 5% Neutral Buffered Formalin for 5 minutes, rinsed in distilled water to remove formalin and then mounted in aquamount for fluorescent visualization using a Zeiss Axioskop Microscope with a FITC filter.

Lack of Penetration of Topically Applied Formulated Antisense Oligonucleotides in Hairless Mouse Skin.

Two main techniques were used for visualizing ASO distribution in skin after topical application. ISIS 13920 is a 2'-MOE ASO that is strongly recognized by the 2E1 monoclonal antibody, facilitating interpretation of IHC staining patterns. ISIS 18073 is a fluorescently labeled ASO and visualization of the fluorescent probes is a direct readout of ASO localization. Both these compounds are 20 mer 2'-O-methoxy-ethyl Antisense oligonucleotides. Initial observations showed a difference in localization pattern of Antisense oligonucleotides in topical formulations when applied to hairless SKH1 vs Balb/c mice. To investigate this further, 5% ASO cream was topically applied to hairless mice. The mice were sacrificed the mice at different time points. The skin was harvested and ASO localization was studied either by immunohistochemistry (FIG. 1A) or fluorescence microscopy (FIG. 1B). Topical administration of cream containing 5% ASO to hairless mice skin for different time points (0, 3 h, 24 h) resulted in no visible staining of either the dermis or epidermis (FIG. 1A). To confirm the immunohistochemistry data by another method of detection, we also applied FITC-labeled Antisense oligonucleotides similarly formulated to hairless mouse skin and again there was no visible staining of epidermis and dermis. Interestingly, we saw ASO distribution in what appears to be hair follicles at about 3 hours (FIG. 1B). It is known that hairless mice have hair follicles but they are not well developed and fully functional (Lauer et al. 1997). However, at 24 hours there was no significant distribution of ASO in epidermis or dermis.

Topically Applied Formulated Antisense Oligonucleotides Accumulates in the Dermis of Balb/C Mice in a Time-Dependant Manner.

It was observed that if the above experiment was repeated in Balb/C mice, the results were very different. Similar to above, 100 µl of the topical cream formulation was applied to hair-clipped Balb/c mouse skin for different periods of time and the skin was harvested and analyzed for ASO distribution by immunohistochemistry and fluorescence microscopy-Intense staining of the dermis was observed in these treatment groups suggesting that Antisense oligonucleotides trafficked through the stratum corneum and was distributed in the dermis. Following the observations above, the kinetics of localization of formulated antisense oligonucleotides were analyzed to determine if a follicular pathway was being used.

Figure 2:
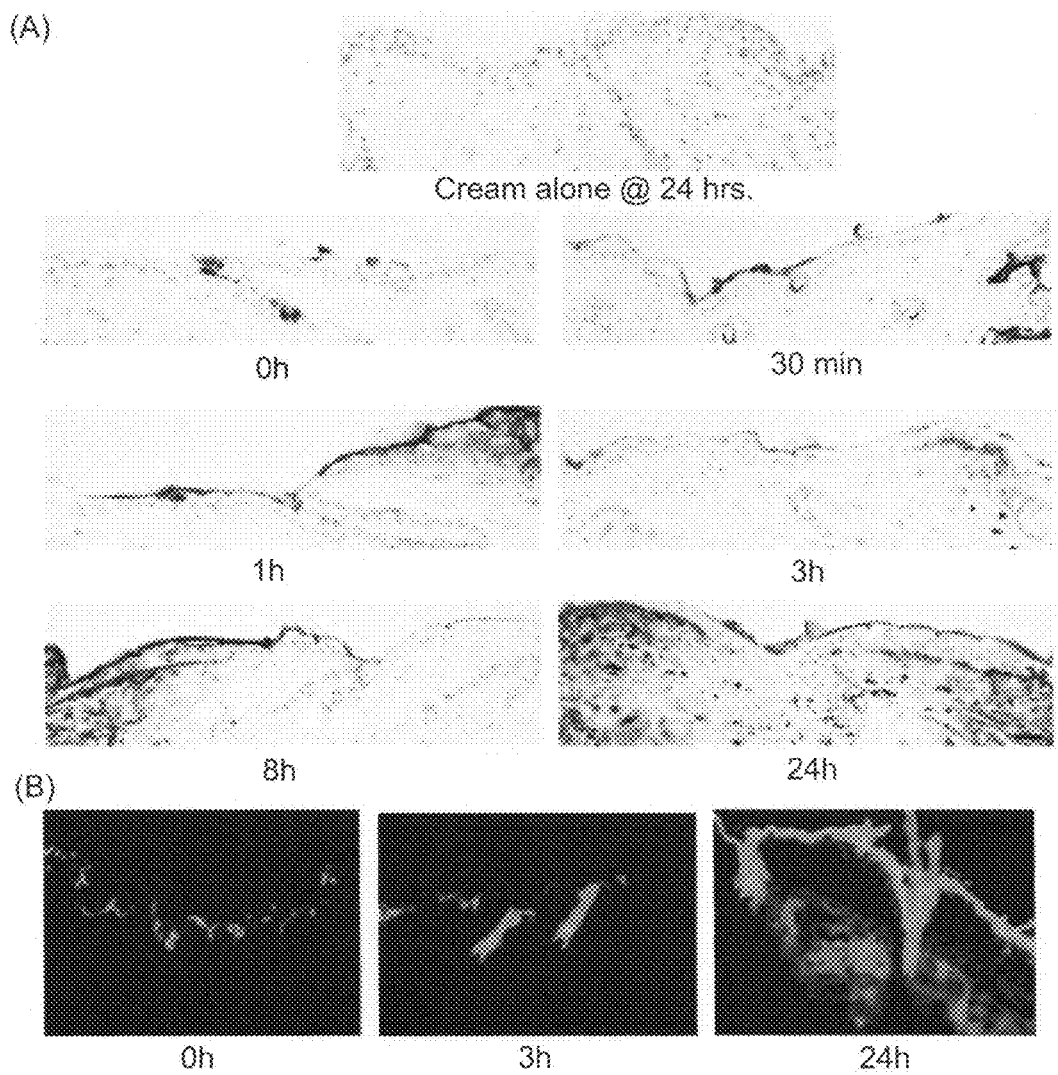
FIG. 2 shows topical nucleic acid distribution after administration of cream to hairy mouse skin. (A) Immunohistochemical photomicrographs of 5% ISIS 13920 cream formulation applied onto hair-clipped Balb/c mouse skin at 0 h, 30 mins, 1 h, 3 h, 8 h, and 24 h. Pictures taken at 20× magnification under Zeiss Axiolab microscope. Scale bar: 20 µm (B) FITC photomicrographs after topical application of 5% ISIS 18073 cream formulation onto hair-clipped Balb/c mouse skin at 0 h, 3 h, and 24 h. Pictures taken at 40× magnification under Zeiss Axiolab microscope. Three animals were evaluated for each group. The micrographs show a representative section from one animal.

Hair-clipped Balb/C mice were treated with the ASO cream formulation for different periods of time (0 h, 30 mins, 1 h, 3 h, 8 h, 24 h) and the skin was harvested for detection by immunohistochemistry. The data (FIG. 2A) demonstrate that antisense oligonucleotides distribute into the skin in a time-dependent manner. At around 3 hours, diffusion of antisense oligonucleotides in the dermis occurs, and this accumulation of antisense oligonucleotide increases over the period of 24 hours. Follicular distribution can be observed as early as 30 minutes after application. The data with FITC-labeled antisense oligonucleotide formulation (FIG. 2B) are consistent with these observations. Additionally, it may be noted that there was an intense fluorescent signal in the dermis with much less fluorescence associated with the epidermis (FIG. 2B). Formulation of the antisense oligonucleotide with a penetration enhancer(s) that favor epidermal penetration can be used to direct the oligonucleotide to that portion of the skin. Hair follicles were defined by accumulation of FITC-antisense oligonulceotide at 3 h, at time when dermal penetration was not yet apparent. Collectively, these data suggest that Antisense oligonucleotides access the dermis via a follicular pathway.

Topically Applied Formulated ASO and Not Simple Saline Formulations Accumulates in the Dermis of Balb/c Mouse Skin.

Figure 3:
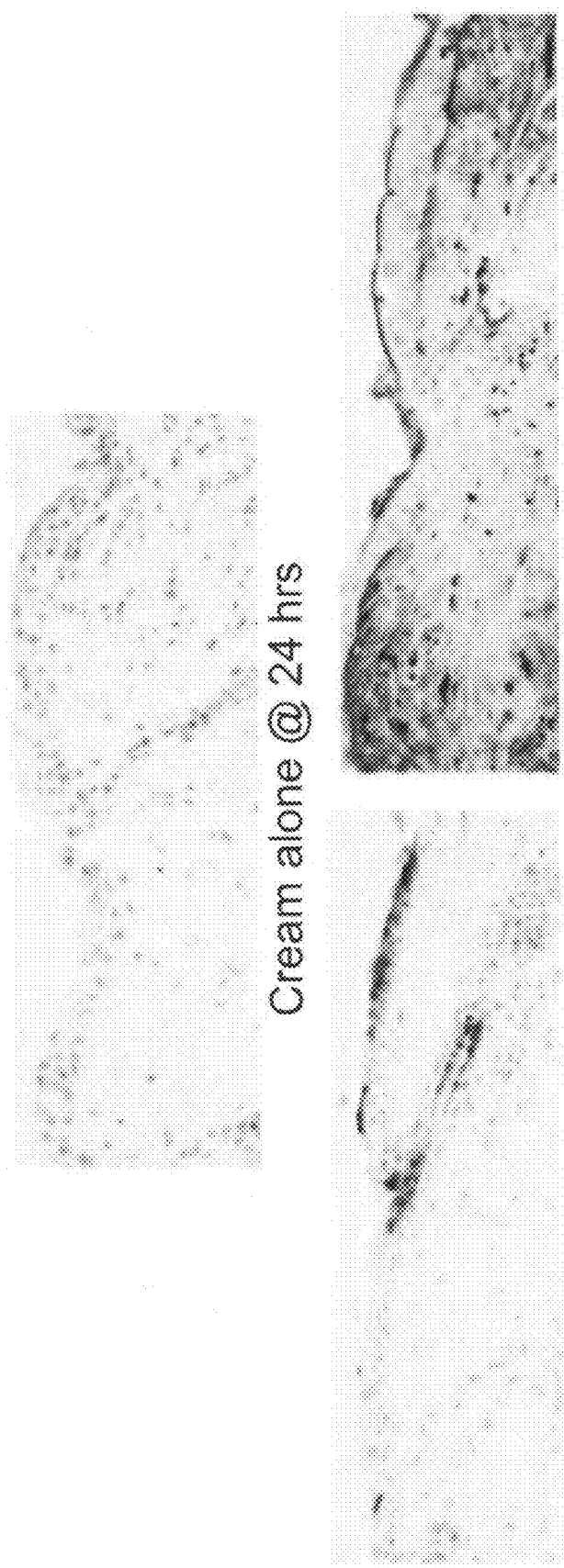
FIG. 3 shows a nucleic acid in a cream formulation, but not in saline, is localized in the dermis of hairy mouse skin. Immunohistochemical photomicrographs of 5% ISIS 13920 cream formulation or ISIS 5% saline formulation applied onto hair-clipped Balb/c mouse skin. Pictures taken at 20× magnification under Zeiss Axiolab microscope. Three animals were evaluated for each group. The micrographs show a representative section from one animal. Scale bar: 20 µm.

To study whether the formulation helped Antisense oligonucleotides distribute into the dermis of Balb/C mice, we also topically applied a simple saline formulation (5% ASO dissolved in saline). Interestingly, while there seemed to be localization of ASO in the hair follicles after 24 h, there was no accumulation of ASO in the dermis when the saline formulation was used (FIG. 3). These data suggest that the penetration enhancer in the cream formulation is required to support the trafficking of the ASO from the hair follicle to the dermis.

Example 7

Method of delayed release of nucleic acid from hair follicles. A two step formulation is used for delayed release of oligonucleotides from the hair follicles into other portions of the skin. The nucleic acid is applied to the skin, preferably skin with a relatively high density of hair follicles. Sufficient time is allowed for the nucleic acid to enter the hair follicles. At the desired time of release of the nucleic acid from the hair follicles into other portions of the skin, a lipophilic compound or penetration enhancer is applied to the skin in the same location where the nucleic acid was applied.

This method can also be used to deliver an increased concentration of the nucleic acid to the dermis and epidermis. The nucleic acid in the aqueous solution is applied to the skin, preferably in an area of relatively high hair follicle density. Sufficient time is allowed for all of the nucleic acid to enter the hair follicles. These steps are repeated to increase concentration of nucleic acid in the hair follicle as desired. The lipophilic compound or penetration enhancer is then applied to the same area of the skin where the nucleic acid was applied.

Example 8

Method for systemic delivery of nucleic acids by topical administration. A formulation comprising a nucleic acid and a dermal penetration enhancer is prepared and applied to an area of the skin having a relatively high density of hair follicles. The formulation may be reapplied until the desired dose is reached. The level of nucleic acid delivered systemically is typically determined by levels of nucleic acid in the serum or other methods known to those skilled in the art. Methods for determination of nucleic acid levels in the skin are well known to those skilled in the art.

Example 9

Method for hair removal comprising administration of nucleic acids preferentially to hair follicles. A formulation comprising a nucleic acid in an aqueous solution, preferably saline, is used to deliver nucleic acids preferentially to hair follicles. The use of nucleic acid molecules to modulate expression of genes and/or proteins in cells has been discussed above. The nucleic acid to be delivered can be a single stranded or double stranded nucleic acid that inhibits expression of a gene or protein by any mechanism of action.

Inhibition of a number of different genes can result in hair loss. A leading candidate gene to target is sonic hedgehog (Shh) or the downstream transcription factor Gli-2 that regulate Shh signaling. The hedgehog pathway is critical for hair follicle epithelial cell growth in the bulge region that regulates the hair cycle (St-Jacques, B et al., *Curr Biol* 8: 1058-1068, 1998; Mill, P et al., *Genes Dev* 17: 282-294, 2003). Gasdermin-3 was identified as the common target of two different mutations resulting in hairless phenotypes in mice (Lunny D P et al., *J Invest Dermatol* 124:615-621, 2005). RBP-J, a protease that cleaves the Notch family of receptors following ligand engagement and regulates cell fate in the hair follicle epithelium, is an attractive target, as well (Yamamoto, N et al., *Curr Biol* 13:333-338, 2003). Conditional ablation of RBP-J produced hair loss in mice, although epidermal cyst formation was also observed.

Hair growth may also be reduced or inhibited by inhibition of ornithine decarboxlyase (ODC), heparanase, and the Vitamin D receptor. ODC is a key enzyme in polyamine synthesis implicated in the anagen phase of the follicular growth cycle (Nancarrow, M J et al., *Mech Dev* 84:161-164, 1999). Heparanase has been demonstrated to enhanced hair growth observed in transgenic mice following chemotherapy-induced hair loss and its expression pattern in bulge keratinocytes suggests a utility in modulation of hair growth (Zcharia, E et al., *Am J Pathol* 166: 999-1008, 2005). Vitamin D receptor deficient mice display an alopecia-like phenotype and skin-specific rescue of hair growth can be achieved by a human Vitamin D transgene in this genetic background (Kong, J et al., *J Invest. Derm.* 118:631-638, 2002). Mice carrying a mutation in the hairless (hr) locus undergo rapid onset postnatal wave of hair shedding beginning at the age of 13-14 days. The hairless phenotype in mice is characterized by similar clinical and histological features in a rare form of human baldness (Djabali et al, *J. Cell Sci.* 114:367-376).

The gene targets listed herein are examples and are not intended to serve as a limitation or exhaustive list.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

It is intended that each of the patents, applications, printed publications, and other published documents mentioned or referred to in this specification be herein incorporated by reference in their entirety.

What is claimed is:

1. A method for delivering an oligonucleotide preferentially to a hair follicle comprising:
   identifying a subject having skin comprising hair follicles;
   selecting a portion of skin comprising hair follicles on said subject for delivery of said oligonucleotide preferentially to hair follicles; and
   delivering a composition comprising an oligonucleotide in an aqueous solution to said portion of skin, wherein the aqueous solution is essentially free of any lipophilic compound or penetration enhancer, wherein said portion of skin is not pretreated with a penetration enhancer, and wherein skin adjacent to said hair follicles which is not part of said hair follicles provides a permeability barrier to said oligonucleotide such that said oligonucleotide preferentially accumulates in a dermal portion of said hair follicles as compared to a dermal layer of said skin adjacent to said hair follicles which is not part of said hair follicles.

2. The method of claim 1, wherein the aqueous solution is normal saline.

3. The method of claim 1, wherein the oligonucleotide is about 8 to about 100 nucleotides in length.

4. The method of claim 1, wherein the oligonucleotide is about 8 to about 80 nucleotides in length.

5. The method of claim 1, wherein the oligonucleotide is about 8 to about 30 nucleotides in length.

6. The method of claim 1, wherein the composition modulates expression of a nucleic acid in the hair follicle.

7. The method of claim 1, wherein at least one internucleoside linkage of the oligonucleotide is a modified internucleoside linkage.

8. The method of claim 7, wherein each internucleoside linkage is a phosphorothioate internucleoside linkage.

9. The method of claim 1, wherein at least one nucleoside of the oligonucleotide comprises a modified sugar.

10. The method of claim 9, wherein at least one modified sugar comprises a 2'-O-methoxyethyl.

11. The method of claim 1, wherein at least one nucleobase of the oligonucleotide is a modified nucleobase.

12. The method of claim 11, wherein the modified nucleobase is a 5-methylcytosine.

13. The method of claim 1, wherein the oligonucleotide consists of 20 linked nucleosides.

14. The method of claim 1, wherein the oligonucleotide is a single-stranded oligonucleotide.

15. The method of claim 1, wherein the oligonucleotide is a pharmaceutically acceptable salt.

16. The method of claim 1, further comprising:
   administering a lipophilic compound or penetration enhancer to said area of skin on said subject after said delivery of said composition, in an amount such that said oligonucleotide preferentially accumulated in said hair follicle is released from the hair follicle into said dermal layer of skin adjacent to said hair follicle which is not part of said hair follicle.

17. The method of claim 1, wherein the oligonucleotide comprises:
   a gap segment consisting of linked deoxynucleosides;
   a 5' wing segment consisting of linked nucleosides;
   a 3' wing segment consisting of linked nucleosides;
   wherein the gap segment is positioned between the 5' wing segment and the 3' wing segment and wherein each nucleoside of each wing segment comprises a modified sugar.

18. The method of claim 17, wherein the oligonucleotide comprises:
   a gap segment consisting of ten linked deoxynucleosides;
   a 5' wing segment consisting of five linked nucleosides;
   a 3' wing segment consisting of five linked nucleosides;
   wherein the gap segment is positioned between the 5' wing segment and the 3' wing segment, wherein each nucleoside of each wing segment comprises a 2'-O-methoxyethyl sugar;
   and wherein each internucleoside linkage of said modified oligonucleotide is a phosphorothioate linkage.

19. The method of claim 18, wherein the oligonucleotide consists of 20 linked nucleosides.

20. The method of claim 6, wherein said modulation of expression of a nucleic acid in the hair follicle modulates hair growth.

21. The method of claim 20, wherein said nucleic acid is hairless (hr) gene.

* * * * *